(12) United States Patent
Hayashi et al.

(10) Patent No.: US 7,862,984 B2
(45) Date of Patent: *Jan. 4, 2011

(54) POLYONIUM BORATES AND RADIATION-SENSITIVE COMPOSITION AND IMAGEABLE ELEMENTS CONTAINING SAME

(75) Inventors: Koji Hayashi, Tatebayashi (JP); Jianbing Huang, Trumbull, CT (US)

(73) Assignee: Eastman Kodak Company, Rochester, NY (US)

( * ) Notice: Subject to any disclaimer, the term of this patent is extended or adjusted under 35 U.S.C. 154(b) by 275 days.

This patent is subject to a terminal disclaimer.

(21) Appl. No.: 11/692,255

(22) Filed: Mar. 28, 2007

(65) Prior Publication Data

US 2008/0241754 A1 Oct. 2, 2008

(51) Int. Cl.
*G03C 1/725* (2006.01)

(52) U.S. Cl. ................. 430/287.1; 430/269; 430/270.1; 430/302; 526/239; 564/8; 568/2; 568/3; 568/6

(58) Field of Classification Search ............... 428/32.1, 428/32.21, 195.1
See application file for complete search history.

(56) References Cited

U.S. PATENT DOCUMENTS

| | | | |
|---|---|---|---|
| 6,309,792 B1 | 10/2001 | Hauck et al. | |
| 6,569,603 B2 | 5/2003 | Furukawa | |
| 6,623,910 B2 | 9/2003 | Shimada et al. | |
| 6,723,495 B2 * | 4/2004 | Ray et al. | 430/322 |
| 6,759,177 B2 | 7/2004 | Shimada et al. | |
| 6,787,281 B2 | 9/2004 | Tao et al. | |
| 6,821,583 B2 * | 11/2004 | Shouldice et al. | 428/32.1 |
| 6,893,797 B2 | 5/2005 | Munnelly et al. | |
| 6,899,994 B2 | 5/2005 | Huang et al. | |
| 6,921,620 B2 * | 7/2005 | Hayakawa et al. | 430/157 |
| 7,172,850 B2 * | 2/2007 | Munnelly et al. | 430/270.1 |
| 7,175,969 B1 * | 2/2007 | Ray et al. | 430/278.1 |
| 7,189,494 B2 * | 3/2007 | Knight et al. | 430/281.1 |
| 2003/0017411 A1 | 1/2003 | Shimada et al. | |
| 2003/0118939 A1 | 6/2003 | Munnelly et al. | |
| 2004/0180289 A1 | 9/2004 | Shimada et al. | |

FOREIGN PATENT DOCUMENTS

| | | |
|---|---|---|
| EP | 1079276 | 2/2001 |
| EP | 1449650 | 8/2004 |
| EP | 1 708 023 | 10/2006 |
| EP | 1182033 | 11/2006 |
| JP | 2002-062482 | 2/2002 |
| JP | 2002-062642 | 2/2002 |
| JP | 2002-116539 | 4/2002 |
| WO | 2005-064402 | 12/2004 |

\* cited by examiner

*Primary Examiner*—Daniel M Sullivan
*Assistant Examiner*—Chukwuma O Nwaonicha
(74) *Attorney, Agent, or Firm*—J. Lanny Tucker

(57) ABSTRACT

A radiation-sensitive composition includes a free-radically polymerizable component, an initiator composition capable of generating free radicals sufficient to initiate polymerization upon exposure to imaging radiation, an infrared radiation absorbing compound, and a polymeric binder. The initiator composition includes a unique polyonium borate comprising a polyvalent onium cation with multiple onium moieties and sufficient organic borate counterions to provide a net neutral charge. The radiation-sensitive composition can be used to prepare a negative-working imageable element that is sensitive to suitable imaging infrared radiation, can be imaged at relatively low energy, and can be developed either on-press or off-press.

13 Claims, No Drawings

POLYONIUM BORATES AND RADIATION-SENSITIVE COMPOSITION AND IMAGEABLE ELEMENTS CONTAINING SAME

FIELD OF THE INVENTION

This invention relates to novel polyonium borates and their use in negative-working radiation-sensitive compositions and imageable elements such as negative-working lithographic printing plate precursors. These imageable elements also can be developed either on-press or off-press. The invention also relates to methods of using these imageable elements.

BACKGROUND OF THE INVENTION

Radiation-sensitive compositions are routinely used in the preparation of imageable materials including lithographic printing plate precursors. Such compositions generally include a radiation-sensitive component, an initiator system, and a binder, each of which has been the focus of research to provide various improvements in physical properties, imaging performance, and image characteristics.

Recent developments in the field of printing plate precursors concern the use of radiation-sensitive compositions that can be imaged by means of lasers or laser diodes, and more particularly, that can be imaged and/or developed on-press. Laser exposure does not require conventional silver halide graphic arts films as intermediate information carriers (or "masks") since the lasers can be controlled directly by computers. High-performance lasers or laser-diodes that are used in commercially-available image-setters generally emit radiation having a wavelength of at least 700 nm, and thus the radiation-sensitive compositions are required to be sensitive in the near-infrared or infrared region of the electromagnetic spectrum. However, other useful radiation-sensitive compositions are designed for imaging with ultraviolet or visible radiation.

There are two possible ways of using radiation-sensitive compositions for the preparation of printing plates. For negative-working printing plates, exposed regions in the radiation-sensitive compositions are hardened and unexposed regions are washed off during development. For positive-working printing plates, the exposed regions are dissolved in a developer and the unexposed regions become an image.

Various radiation compositions and imageable elements containing reactive polymer binders are described in U.S. Pat. No. 6,569,603 (Furukawa) and EP 1,182,033A1 (Fujimaki et al.). The reactive polymer binders include reactive vinyl groups that are pendant to the polymer backbone. Other IR-sensitive compositions are described in U.S. Pat. No. 6,309,792 (Hauck et al.), U.S. Pat. No. 6,893,797 (Munnelly et al.), U.S. Pat. No. 6,787,281 (Tao et al.), and U.S. Pat. No. 6,899,994 (Huang et al.), U.S. Patent Application Publication 2003/0118939 (West et al.), and EP 1,079,276A1 (Lifka et al.) and EP 1,449,650A1 (Goto).

Various publications such as U.S. Patent Application Publications 2003/0017411 (Shimada et al.) and 2004/0180289 (Shimada et al.) describe initiator compositions needed to provide free radicals upon imagewise exposure so the imaged (exposed) regions are cured or polymerized so they are insoluble in the alkaline developers. For example, onium salts (including polyvalent onium salts having multiple cation charges and counterions) are used to generate free radicals in the negative-working compositions and elements described in U.S. Pat. No. 6,759,177 (Shimada et al.). U.S. Pat. No. 6,623,910 (Shimada et al.) describes negative-working elements containing onium salts with a counterion having a valency of at least 2.

EP 1,708,023 (Hayashi et al.) describes polyvalent onium salts in its Chemical Formulae 9 and 10 with different cationic groups along with a suitable number of the same counterion.

Problem to be Solved

The various radiation sensitive compositions of the art can readily be used to prepare negative-working imageable elements but they do not always have the desired long press life with small dot gain.

SUMMARY OF THE INVENTION

The present invention provides a polyonium borate comprising a polyvalent onium cation and sufficient organic borate counterions to provide a net neutral charge.

In addition, the present invention provides a radiation-sensitive composition comprising:

a free radically polymerizable component, an initiator composition capable of generating free radicals sufficient to initiate polymerization of the free radically polymerizable component upon exposure to imaging radiation, an infrared radiation absorbing compound, and a polymeric binder, wherein the initiator composition comprises a polyonium borate comprising a polyvalent onium cation and sufficient organic borate counterions to provide a net neutral charge.

This invention further provides a negative-working imageable element comprising a substrate having thereon an imageable layer comprising the radiation-sensitive composition of this invention.

This invention also provides a method comprising:

A) imagewise exposing the imageable element of this invention to produce exposed and non-exposed regions, and B) developing the imagewise exposed element to remove only the non-exposed regions.

The negative-working radiation-sensitive compositions and imageable elements of this invention provide printing plates with long press life with small dot gain. This advantage is achieved by using novel polyonium borates having multiple onium cations.

DETAILED DESCRIPTION OF THE INVENTION

Definitions

Unless the context indicates otherwise, when used herein, the terms "polyonium borates", "radiation-sensitive composition", "imageable element", "lithographic printing plate precursor", and "printing plate precursor" are meant to be references to embodiments of the present invention.

In addition, unless the context indicates otherwise, the various components described herein such as "radically polymerizable component", "polyonium borate", "co-initiator", "infrared radiation absorbing compound", "polymeric binder", "nonionic phosphate (meth)acrylate", and similar terms also refer to mixtures of such components. Thus, the use of the articles "a", "an", and "the" is not necessarily meant to refer to only a single component.

The term "single-layer imageable element" refers to an imageable element having only one imageable layer that is essential to imaging, but as pointed out in more detail below, such elements may also include one or more layers under or over (such as a topcoat) the imageable layer to provide various properties.

The term "negative-working" has the meaning conventional in the art, whereby imaged (exposed) regions of the radiation-sensitive composition (or imageable layer) in the imageable element are cured or made insoluble in the developer and non-imaged (non-exposed) regions are readily removed using the developer.

Moreover, unless otherwise indicated, percentages refer to percents by dry weight.

For clarification of definitions for any terms relating to polymers, reference should be made to "Glossary of Basic Terms in Polymer Science" as published by the International Union of Pure and Applied Chemistry ("IUPAC"), *Pure Appl. Chem.* 68, 2287-2311 (1996). However, any definitions explicitly set forth herein should be regarded as controlling.

"Graft" polymer or copolymer refers to a polymer having a side chain that has a molecular weight of at least 200.

The term "polymer" refers to high and low molecular weight polymers including oligomers and includes homopolymers and copolymers.

The term "copolymer" refers to polymers that are derived from two or more different monomers.

The term "backbone" refers to the chain of atoms in a polymer to which a plurality of pendant groups are attached. An example of such a backbone is an "all carbon" backbone obtained from the polymerization of one or more ethylenically unsaturated polymerizable monomers. However, other backbones can include heteroatoms wherein the polymer is formed by a condensation reaction or some other means.

Uses

The polyonium borates can be used in a number of ways. For example, they can be used in any free radical-curable coating or formulation that may be used for automotive and appliance coatings and as paint compositions and printing ink compositions. In addition, they can be used to provide photoresists liquid crystal displays, color filters, and plasma displays. In many embodiments of this invention described below, they can be used to produce free radicals that are needed for free radical polymerization of polymerizable compositions, such as radiation-sensitive compositions that can be used as hardenable or curable coatings. For example, radiation-sensitive compositions containing the polyonium borates can be hardened or cured in response to imaging radiation for various uses described below. Negative-working lithographic printing plate precursors are examples of imageable elements containing the polyonium borates as free radical generating compounds.

Polyonium Borates

The unique compounds of this invention that have the various uses described above are polyonium borates, each comprising a polyvalent onium cation and sufficient organic borate counterions to provide a net neutral charge for each salt. By "polyvalent onium", we mean that the onium cation has two or more cationic charges provided by the same or different onium moieties, such moieties including but not limited to divalent halonium (such as iodonium), trivalent sulfonium, tetravalent phosphonium, and tetravalent diazonium moieties. Thus, in some embodiments, each polyvalent onium cation has multiple charges from the same onium moiety, but in other embodiments, the polyvalent onium cation has a mixture of two or more different onium moieties, such as one or more iodonium moieties and one or more sulfonium moieties in the same cation. The upper limit of onium moieties in a given polyvalent onium cation is limited only by what is practical and synthetically possible. In most embodiments, there are two to five of the same or different positive charges (onium moieties) per polyvalent onium cation, but in still other embodiments, there are two or three of the same or different positive charges (onium moieties) per polyvalent onium cation.

For example, the polyonium borate of this invention can include a polyvalent onium cation that is a polyiodonium cation (with two or more iodonium moieties), polysulfonium cation (with two or more sulfonium moieties), polyphosphonium cation (with two or more phosphonium moieties), or polydiazonium cation (with two or more diazonium moieties). Alternatively, a single polyonium cation can comprise two or more different iodonium and two or more sulfonium moieties, or two or more phosphonium moieties and two or more diazonium moieties, or similar combinations. Polyonium cations are useful with the same or different borate counterions as described below.

Each polyonium borate compound has a net neutral charge, with the positive charges of the polyvalent onium cation being balanced the same number of borate anions.

Representative polyonium borates can be represented by the following Structures (I) through (IV):

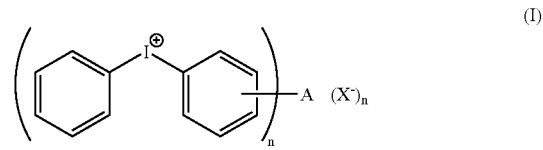

(I)

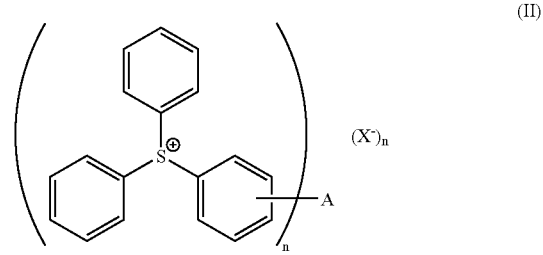

(II)

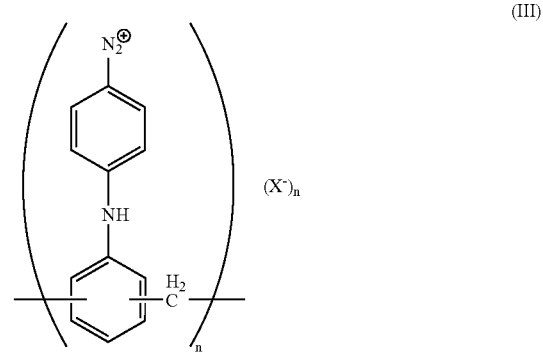

(III)

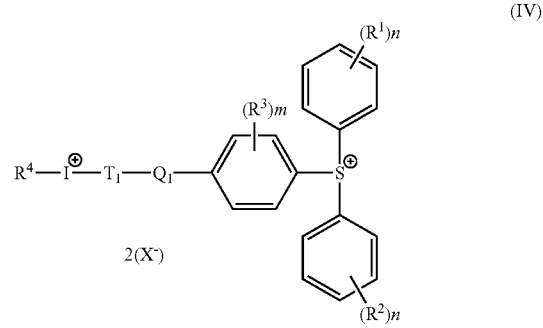

(IV)

wherein n is at least 2 (typically 2, 3, or 4), A represents (n−1) connecting groups (such as a single bond where n is 2), a substituted or unsubstituted divalent aliphatic group n is 2, or a trivalent substituted or unsubstituted aliphatic group when n is 3. Such aliphatic connecting groups can include 1 to 20 carbon, nitrogen, sulfur, or oxygen atoms in the chain connecting the onium moieties.

In Structure IV above, $R^1$ to $R^3$ are independently halogen atoms, substituted or unsubstituted alkyl groups having 1 to 20 carbon atoms, substituted or unsubstituted haloalkyl groups having 1 to 20 carbon atoms, substituted or unsubstituted aryl groups having 6 or 10 carbon atoms in the aromatic rings, substituted or unsubstituted alkoxy groups having 1 to 20 carbon atoms, substituted or unsubstituted aryloxy groups having 6 or 10 carbon atoms in the aromatic rings, alkylthio groups having 1 to 20 carbon atoms in the alkyl groups, arylthio groups having 6 or 10 carbon atoms in the aromatic rings, or primary, secondary, or tertiary amino groups, all of which may be further substituted. $Q_1$ is a direct linkage, an oxygen atom, a sulfur atom, or a lower substituted or unsubstituted alkylene chain (having 1 to 6 carbon atoms). $T_1$ is an alkylene group (having 1 to 6 carbon atoms) or an arylene group (having 6 or 10 carbon atoms in the ring), each of which may have one or more substituents that are halogen atoms, alkyl groups, haloalkyl groups, aryl groups, alkoxy groups, aryloxy groups, alkylthio groups, arylthio groups, and amino groups that may be further substituted. $R^4$ is a substituted or unsubstituted alkyl group (having 1 to 20 carbon atoms), a substituted or unsubstituted alkenyl group (having 2 to 20 carbon atoms), a substituted or unsubstituted aryl group (having 6 or 10 carbon atoms in the aromatic ring), or a substituted or unsubstituted alkylaryl group (having at least 7 carbon atoms), all of which may be further substituted with halogen atoms, alkyl groups, haloalkyl groups, aryl groups, alkoxy groups, aryloxy groups, alkylthio groups, arylthio groups, or amino groups all of which may be further substituted.

Also, in Structure IV, m is an integer of 0 to 4 and the two n's are independently 0 or integers of 1 to 5.

Alternatively, $R^4$ can be a group represented by the following general Structure (IV-A):

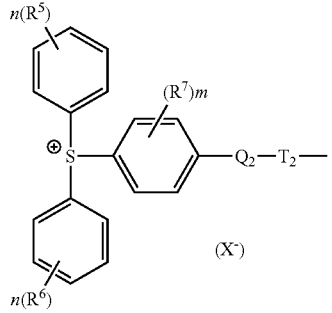

(IV-A)

wherein $R^5$ to $R^7$ are independently halogen atoms, substituted or unsubstituted alkyl groups independently having 1 to 20 carbon atoms, substituted or unsubstituted haloalkyl groups each having 1 to 20 carbon atoms, substituted or unsubstituted aryl groups each having 6 or 10 carbon atoms in the aromatic ring, substituted or unsubstituted alkoxy groups each having 1 to 20 carbon atoms, substituted or unsubstituted aryloxy groups each having 6 or 10 carbon atoms in the aromatic ring, substituted or unsubstituted alkylthio groups each having 1 to 20 carbon atoms in the alkyl groups, substituted or unsubstituted arylthio groups each having 6 or 10 carbon atoms in the aromatic ring, or primary, secondary, or tertiary amino groups that may be substituted with substituents defined above for $R^1$ to $R^3$. $Q_2$ is a direct linkage, an oxygen atom, a sulfur atom, or a substituted or unsubstituted lower alkylene chain having 1 to 6 carbon atoms. $T_2$ a substituted or unsubstituted alkylene (having 1 to 6 carbon atoms) or arylene group (having 6 or 10 carbon atoms in the aromatic ring) that may have one or more substituents such as halogen atoms, alkyl groups, haloalkyl groups, aryl groups, alkoxy groups, aryloxy groups, alkylthio groups, arylthio groups, or amino groups that may be further substituted. In addition, in Structure IV-A, m is an integer of 0 to 4 and the two n's are independently 0 or an integer of 1 to 5.

Any of the phenyl rings in Structures (I) through (IV) can be substituted with one or more substituents that would be readily apparent to one skilled in the art that would not interfere with the desired properties of the polyonium borate. Such substituents include but are not limited to halogen atoms, alkyl groups, haloalkyl groups, aryl groups, alkoxy groups, aryloxy groups, alkylthio groups, arylthio groups, or amino groups. In addition, two more substituents on the same or adjacent phenyl rings may be combined to form aromatic fused rings with the main phenyl rings.

In the noted Structures (I) through (IV) and (IV-A), $X^-$ represents the same or different organic borate counterions that typically comprise same or different polyalkyl-, polyaryl-, or alkylarylborate cations, all of which can be unsubstituted or substituted with one or more groups that would not adversely affect the properties of the polyonium borate. For example, the aryl moieties in the borate counterions can be substituted with one or more alkyl (such as methyl, ethyl, iso-propyl, and t-butyl), alkoxy (similarly to the alkyl groups), halo, or halomethyl groups (such as one or more fluoro, chloro, or trifluoromethyl groups). The various alkyl, aryl, and alkylaryl substituents in the borate counterions can be substituted or unsubstituted and have at least 1 carbon atom (for the alkyl groups), at least 6 carbon atoms in the aryl rings, and at least 7 carbon atoms in the alkylaryl groups.

More particularly, the boron-containing anion or borate counterion can be represented by the following Structure (V):

(V)

wherein $R_1$, $R_2$, $R_3$, and $R_4$ are independently substituted or unsubstituted alkyl groups having 1 to 12 carbon atoms (such as methyl, ethyl, n-propyl, iso-propyl, n-butyl, isobutyl, t-butyl, all pentyl isomers, 2-methylpentyl, all hexyl isomers, 2-ethylhexyl, all octyl isomers, 2,4,4-trimethylpentyl, all nonyl isomers, all decyl isomers, all undecyl isomers, all dodecyl isomers, methoxymethyl, and benzyl), substituted or unsubstituted carbocyclic aryl groups having 6 to 10 carbon atoms in the aromatic ring (such as phenyl, p-methylphenyl, 2,4-methoxyphenyl, naphthyl, 3,5-(trifluoromethyl) phenyl, 4-trifluoromethyl phenyl, 3-trifluoromethyl phenyl, 4-fluoro phenyl, and pentafluorophenyl groups), substituted or unsubstituted alkenyl groups having 2 to 12 carbon atoms (such as ethenyl, 2-methylethenyl, allyl, vinylbenzyl, acryloyl, and crotonotyl groups), substituted or unsubstituted alkynyl groups having 2 to 12 carbon atoms (such as ethynyl, 2-methylethynyl, and 2,3-propynyl groups), substituted or unsubstituted cycloalkyl groups having 3 to 8 carbon atoms in the ring structure (such as cyclopropyl, cyclopentyl, cyclohexyl, 4-methylcyclohexyl, and cyclooctyl groups), or substituted or unsubstituted heterocyclyl groups having 5 to 10 carbon, oxygen, sulfur, and nitrogen atoms (including both aromatic and non-aromatic groups, such as substituted or unsubstituted pyridyl, pyrimidyl, furanyl, pyrrolyl, imidazolyl, triazolyl, tetrazoylyl, indolyl, quinolinyl, oxadiazolyl, and benzoxazolyl groups). Alternatively, two or more of $R_1$, $R_2$, $R_3$, and $R_4$ can be joined together to form a heterocyclic ring with the boron atom, such rings having up to 7 carbon, nitrogen, oxygen, or nitrogen atoms.

In some embodiments, $R_1$, $R_2$, $R_3$, and $R_4$ are independently substituted or unsubstituted alkyl or aryl groups as defined above, and typically, at least 3 of $R_1$, $R_2$, $R_3$, and $R_4$ are the same or different substituted or unsubstituted aryl groups (such as substituted or unsubstituted phenyl groups). For example, all of $R_1$, $R_2$, $R_3$, and $R_4$ can be the same or different substituted or unsubstituted aryl groups or all of the groups are the same substituted or unsubstituted phenyl group. In other embodiments, the substituents of the borate are all substituted or unsubstituted aryl groups, or one of them is an alkyl, for example, alkyltriarylborates or tetraarylborates.

In still other embodiments, the organic borate counterions comprise the same alkyltriarylborate, dialkyldiarylborate, trialkylarylborate, or tetraarylborate counterions. In yet other embodiments, X⁻ represents the same or different tetraphenyl borates or alkyltriphenyl borates (including the same or different alkyl isomers). Butyltriphenyl borate is one useful cation. Useful polyonium borates include the polyiodonium tetraaryl borates wherein the aryl groups are optionally substituted with the same or different substituents (as defined above).

The polyonium borates of this invention can be used in various applications in amounts that range from at least 0.1 and up to 20% solids, based on the total dry weight of a formulation, radiation-sensitive composition, or imageable element in which it is incorporated. Mixtures of different polyonium borates can be used in which each borate is present at the same or different concentrations. In many embodiments of the radiation-sensitive compositions and imageable elements, the one or more polyonium borates are present in an amount of from about 3 to about 15% solids (based on total dry weight).

The polyiodonium borates represented by Structure (I) noted above can be prepared using known synthetic methods for example as described in U.S. Pat. No. 6,558,871 (Takahashi et al.), according to the representative reaction scheme illustrated below wherein M represents an alkali metal and X⁻ is a borate as described above, "n" and "A" are described above, $R^{1'}$ and $R^{2'}$ are independently halogen atoms, substituted or unsubstituted alkyl groups having 1 to 20 carbon atoms, substituted or unsubstituted haloalkyl groups having 1 to 20 carbon atoms, substituted or unsubstituted aryl groups having 6 or 10 carbon atoms in the aromatic rings, substituted or unsubstituted alkoxy groups having 1 to 20 carbon atoms, substituted or unsubstituted aryloxy groups having 6 or 10 carbon atoms in the aromatic rings, alkylthio groups having 1 to 20 carbon atoms in the alkyl groups, arylthio groups having 6 or 10 carbon atoms in the aromatic rings, or primary, secondary, or tertiary amino groups, all of which may be further substituted. Also, "a" is 0 or an integer of 1 to 5 and "b" is 0 or an integer of 1 to 4. The reaction of compound [1] and compound [2] in the presence of a catalyst (for example, sulfuric acid) is carried out in an organic solvent (such as acetic acid and acetic anhydride, if required) at a temperature of from −20° C. to room temperature for one to ten hours. After completing the reaction, the reaction mixture is added to water and stirred. The resulting compound [3] is either removed by filtration or extracted with an organic solvent, and the desired polyiodonium borate of Structure (I) is obtained using a salt exchange reaction to provide the borate counterion.

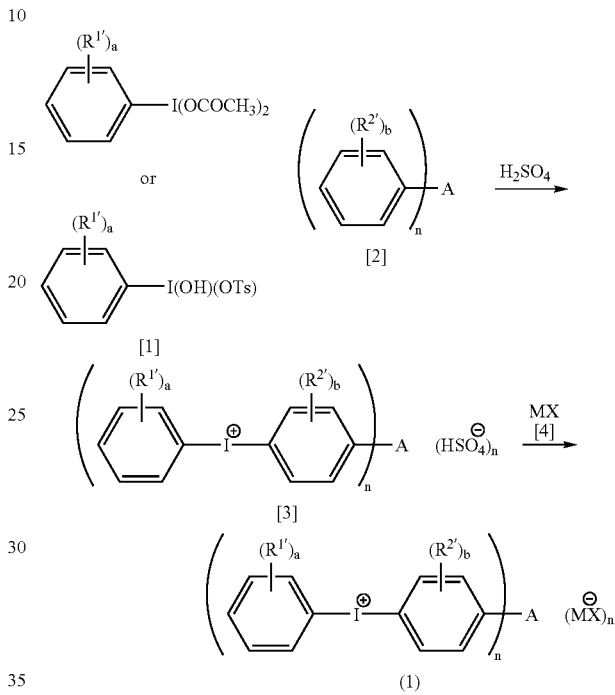

Structure (I) polyiodonium cations can be also prepared by the known synthetic method described in Japanese Kokai 2005-220122A (Touma et al.).

The polysulfonium borates represented by Structure (II) can be synthesized using, for example, any of the following [A], [B] and [C] methods.

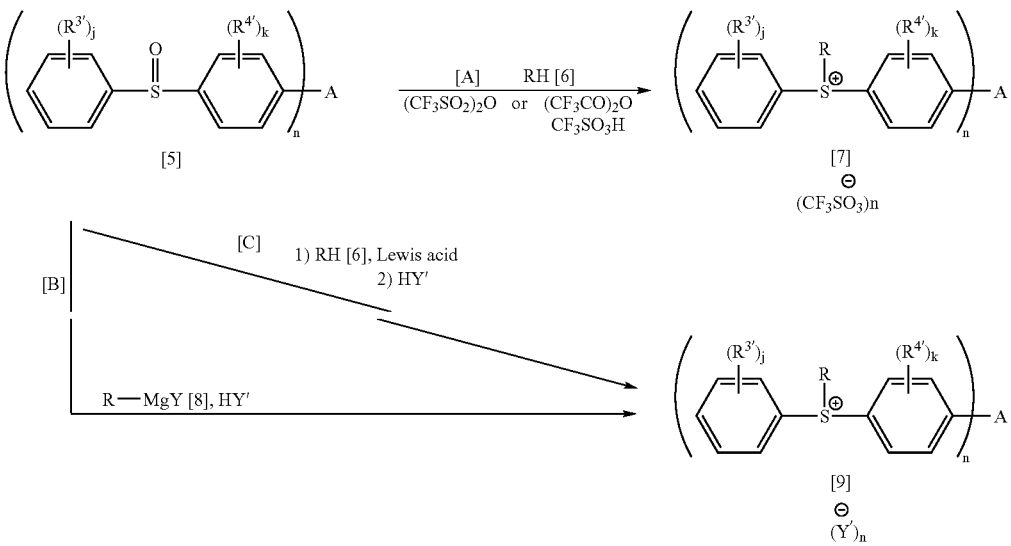

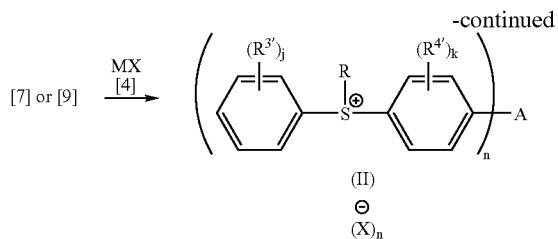

(II)

M is a metal atom, Y and Y' are halogen atoms, X⁻ is a borate as described above, A and "n" are as described above, and R, R³' to R⁴' are independently halogen atoms, substituted or unsubstituted alkyl groups having 1 to 20 carbon atoms, substituted or unsubstituted haloalkyl groups having 1 to 20 carbon atoms, substituted or unsubstituted aryl groups having 6 or 10 carbon atoms in the aromatic rings, substituted or unsubstituted alkoxy groups having 1 to 20 carbon atoms, substituted or unsubstituted aryloxy groups having 6 or 10 carbon atoms in the aromatic rings, alkylthio groups having 1 to 20 carbon atoms in the alkyl groups, arylthio groups having 6 or 10 carbon atoms in the aromatic rings, or primary, secondary, or tertiary amino groups, all of which may be further substituted. Also, "j" is 0 or an integer of 1 to 5 and "k" is 0 or an integer of 1 to 4.

In a method [A], a sulfoxide shown by general formula [5], synthesized by a common method [see Ber., 23, 1844 (1890), J. Chem. Soc. (C), 2424 (1969)] is dissolved in a solvent such as an ether (such as ethyl ether, isopropyl ether, tetrahydrofuran and 1,2-dimethoxyethane) hydrocarbon (such as hexane and heptane), and aromatic hydrocarbons (such as benzene and nitrobenzene) or a mixture of solvents such as one of the above solvent and a halogenated hydrocarbon (such as methylene chloride, methylene bromide, 1,2-dichloroethane and chloroform), along with compound [6] in an amount of 1 to 10 mole parts, (hereinafter in the description on methods [A], [B] and [C], "mole parts" means how many mole parts relative to 1 mole part of a raw compound such as a sulfoxide shown by the general formula [5]). Trifluoromethanesulfonic anhydride in an amount of 1 to 3 mole parts of, or trifluoromethane sulfonic acid in an amount of 1 to 3 mole parts, and trifluoroacetic anhydride in an amount of 1 to 3 mole parts, relative to the sulfoxide shown by the general formula [5], are added thereto at −80 to 30° C., and reaction is allowed to take place at −80 to 30° C. for 0.5 to 10 hours with stirring to obtain a compound shown by the general formula [7]. After completing the reaction, the reaction mixture is added to water and stirred. The resulting compound [7] is either removed by filtration or extracted with an organic solvent such as methylene chloride, 1,2-dichloroethane, ethyl acetate, butyl acetate, propylene glycol monomethyl ether acetate, methyl isobutyl ketone, and the desired polysulfonium borate of Structure (II) is obtained using a borate exchange reaction in a solvent mixture of water and an alcohol such as methanol, ethanol, or propanol to provide the borate counterion.

In a method [B], a sulfoxide shown by the general formula [5] is dissolved in an ether such as ethyl ether, isopropyl ether, tetrahydrofuran, or 1,2-dimethyl ether or a mixture of an ether and a halogenated hydrocarbon such as methylene chloride, methylene bromide, 1,2-dichloroethane and chloroform or an aromatic hydrocarbon such as benzene, toluene and xylene. The Grignard reagent (RMgX) in an amount of 0.5 to 3 mole parts, shown by general formula [8] is added thereto, if necessary, in the presence of a catalyst such as trimethylsilyl triflate and trimethylsilyl chloride at −70 to 50° C., and allowing reaction at −70 to 50° C. for 0.5 to 10 hours with stirring. After completion of the reaction, the reaction solution is treated with an aqueous solution of hydrohalic acid (HX') such as an aqueous solution of hydrobromic acid, hydrochloric acid, or hydroiodic acid to obtain a compound shown by general formula [9]. After completing the reaction, the reaction mixture is added to water and stirred. The resulting compound [9] is either removed by filtration or extracted with an organic solvent such as methylene chloride, 1,2-dichloroethane, ethyl acetate, butyl acetate, propylene glycol monomethyl ether acetate, methyl isobutyl ketone, and the desired polysulfonium borate of Structure (II) is obtained using a borate exchange reaction in a solvent mixture of water and an alcohol such as methanol, ethanol, or propanol to provide the borate counterion.

In method [C], compound [5] is reacted with a compound shown by the general formula [6] in an amount of 1 to 50 mole parts and a Lewis acid such as a halogenated aluminum (for example, aluminum chloride, aluminum bromide and aluminum iodide), a halogenated boron (for example, boron trifluoride and boron tribromide) and a trihalogenated metal (for example, iron trichloride, iron tribromide, titanium tribromide, titanium trichloride, and titanium tribromide) in an amount of 1 to 10 mole parts at −20 to 180° C. for 0.5 to 24 hours with stirring, followed by treating with an aqueous solution of hydrohalic acid (HX) noted above to obtain compound [9]. After completing the reaction, the reaction mixture is added to water and stirred. The resulting compound [9] is either removed by filtration or extracted with an organic solvent such as methylene chloride, 1,2-dichloroethane, ethyl acetate, butyl acetate, propylene glycol monomethyl ether acetate, methyl isobutyl ketone, and the desired polysulfonium borate of Structure (II) is obtained using a borate exchange reaction in a solvent mixture of water and an alcohol such as methanol, ethanol, or propanol to provide the borate counterion.

Polysulfonium borates represented by Structure (II) also can be obtained by using the described methods [A], [B] and [C] using a di(sulfonyl phenyl) compound such as bis-4-(sulfonyl phenyl)diphenyl methane, which may be commercially available or suitably synthesized using known reactants and reaction conditions, as the starting material.

Polydiazonium borates represented by Structure (III) noted above can be prepared using common synthetic methods, for example the synthetic methods described in Photo. Sci. Eng., 17, 33 (1973), U.S. Pat. Nos. 2,063,631 (Schmidt et al.) and 2,679,498 (Seven et al.) and Japanese Kokoku 1974-45322B (Gillich et al.) and 1974-45323B (Steppan et al.), and using the general reaction scheme illustrated below, wherein M represents an alkali metal, X⁻ is a borate as described above, and "n" is as described above. The reaction of a p-diazodiphenylamine, shown by compound [10] and formaldehyde, shown by compound [11], with a catalyst, sulfuric acid, is carried out at a temperature of 0° C. for several hours. After completing the reaction, the reaction solution is added to water and stirred. The resulting precipitated compound can be taken out by filtration and p-diazo-diphenylamineformaldehyde co-condensate resin hydrosulfuric acid salt, shown by general formula [12], is obtained.

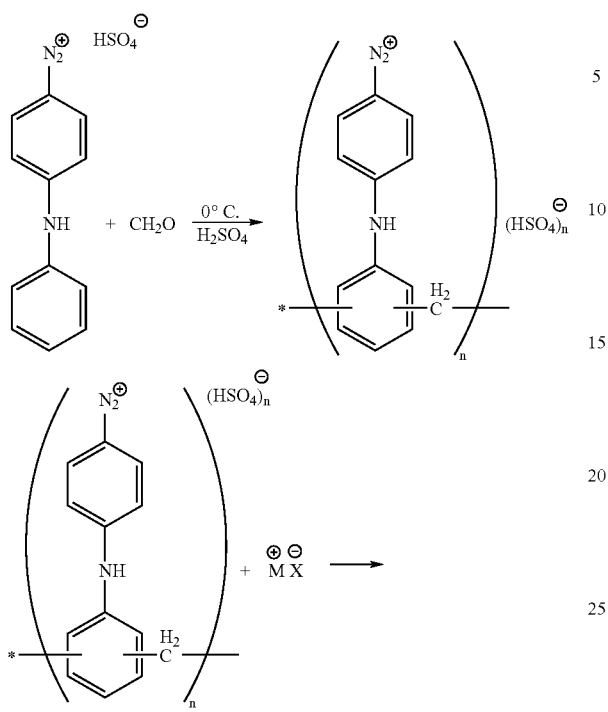

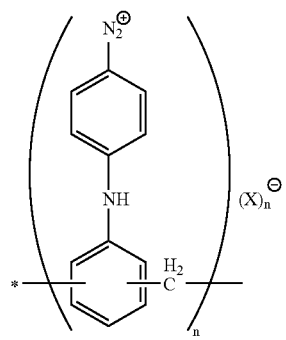

This resin, shown by general formula [12], is dissolved in an appropriate organic solvent such as ethyleneglycol monomethylether, and a borate salt solution is added to exchange the ion pair. After completing the reaction, the reacted solution is added to water and stirred. The resulting precipitated polydiazonium borate can be removed by filtration.

The polyonium borates represented by Structure (IV) can be prepared using the following general synthetic procedure:

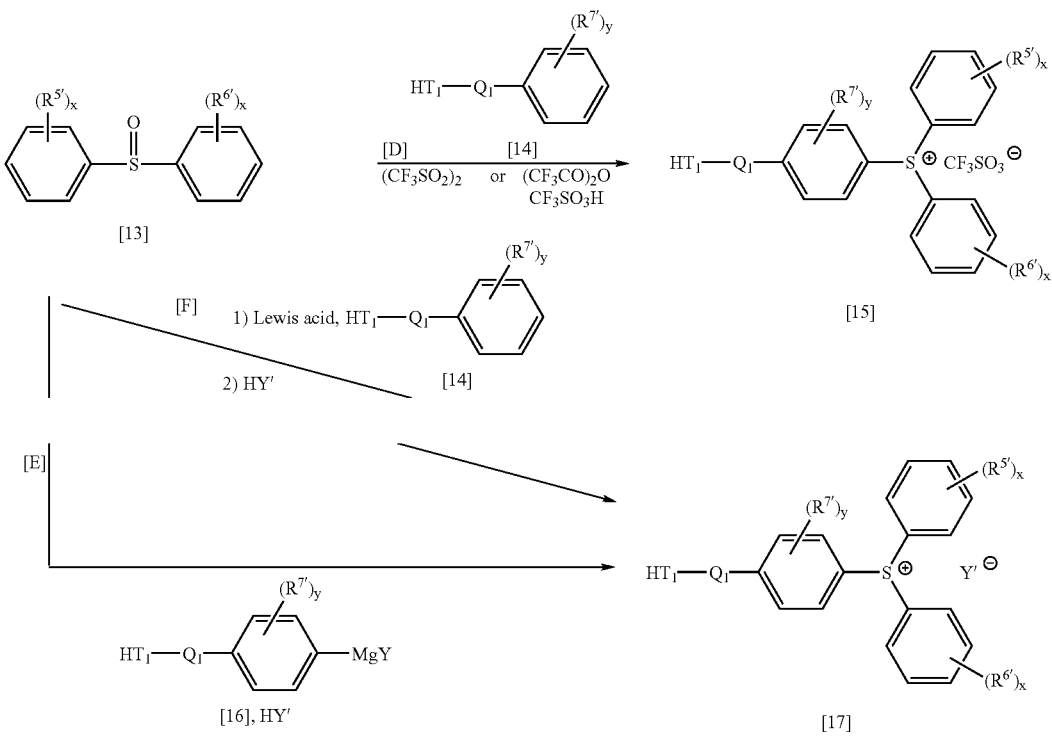

The sulfonium salt shown by the general formula [20] can be synthesized, for example, by the following methods [D], [E], [F] (wherein Y and Y' are each independently a halogen atom, M is a metal atom, and R, $R^{5'}$ to $R^{7'}$ are independently halogen atoms, substituted or unsubstituted alkyl groups having 1 to 20 carbon atoms, substituted or unsubstituted haloalkyl groups having 1 to 20 carbon atoms, substituted or unsubstituted aryl groups having 6 or 10 carbon atoms in the aromatic rings, substituted or unsubstituted alkoxy groups having 1 to 20 carbon atoms, substituted or unsubstituted aryloxy groups having 6 or 10 carbon atoms in the aromatic rings, alkylthio groups having 1 to 20 carbon atoms in the alkyl groups, arylthio groups having 6 or 10 carbon atoms in the aromatic rings, or primary, secondary, or tertiary amino groups, all of which may be further substituted. Also, "x" is 0 or an integer of 1 to 5 and "y" is 0 or an integer of 1 to 4. $Q_1$ and $T_1$ are the same as described above). The halogen atom shown by Y and Y' includes, for example, a fluorine atom, a chlorine atom, a bromine atom, or an iodine atom. The metal atom shown by M includes, for example, a lithium atom, a sodium atom, a potassium atom, a rubidium atom, a silver atom, or a cesium atom.

The compound shown by the general formula [13] may be a commercial product or one suitably synthesized in accordance with a known method. The Grignard reagent shown by the general formula [16] may be one suitably synthesized in accordance with a common method.

In method [D], a sulfoxide shown by the general formula [13], synthesized by a common method [for example, see Ber., 23, 1844 (1890) and J. Chem. Soc.(C), 2424 (1969)] is dissolved in a solvent such as ethers including ethyl ether, isopropyl ether, tetrahydrofuran, and 1,2-dimethoxyethane, hydrocarbons including hexane and heptane, or aromatic hydrocarbons including benzene and nitrobenzene, or a mixed solvent consisting of the above solvent and halogenated hydrocarbons including methylene chloride, methylene bromide, 1,2-dichloroethane, and chloroform. A compound shown by the general formula [14] in an amount of 1 to 10 mole parts, trifluoromethanesulfonic anhydride in an amount of 1 to 3 mole parts or trifluoromethanesulfonic acid in an amount of 1 to 3 mole parts and trifluoroacetic anhydride in an amount of 1 to 3 mole parts, relative to 1 mole part of the sulfoxide shown by the general formula [13] are added thereto at −80 to 30° C., followed by allowing a reaction to take place at −80 to 30° C. for 0.5 to 10 hours with stirring, whereby the compound shown by the general formula [15] is obtained.

In method [E], a compound shown by the general formula [13] is dissolved in ethers such as ethyl ether, isopropyl ether, tetrahydrofuran, and 1,2-dimethoxy ethane, or a mixed solvent consisting of the above ethers and halogenated hydrocarbons such as methylene chloride, methylene bromide, 1,2-dichloroethane and chloroform and aromatic hydrocarbons such as benzene, toluene and xylene, and a Grignard reagent shown by the general formula [16] in an amount of 0.5 to 3 mole parts relative to 1 mole part of the compound shown by the general formula [13] is added thereto, if necessary, in the presence of a catalyst such as trimethylsilyl triflate or, trimethylsilyl chloride, at −70 to 50° C., followed by allowing a reaction to take place at −70 to 50° C. for 0.5 to 10 hours with stirring. After completion of the reaction, the reaction solution is treated with an aqueous solution of hydrohalic acid (HX') such as an aqueous solution of hydrobromic acid, hydrochloric acid or hydroiodic acid to obtain a compound shown by the general formula [17].

In method [F], a compound shown by the general formula [13] is reacted with a compound shown by the general formula [14] in an amount of 1 to 50 mole parts and Lewis acid in an amount of 1 to 10 mole parts, relative to 1 mole part of said compound at −20 to 180° C. for 0.5 to 24 hours with stirring, followed by treating with an aqueous solution of hydrohalic acid (HX') such as an aqueous solution of hydrobromic acid, hydrochloric acid or hydroiodic acid to obtain a compound shown by the general formula [17].

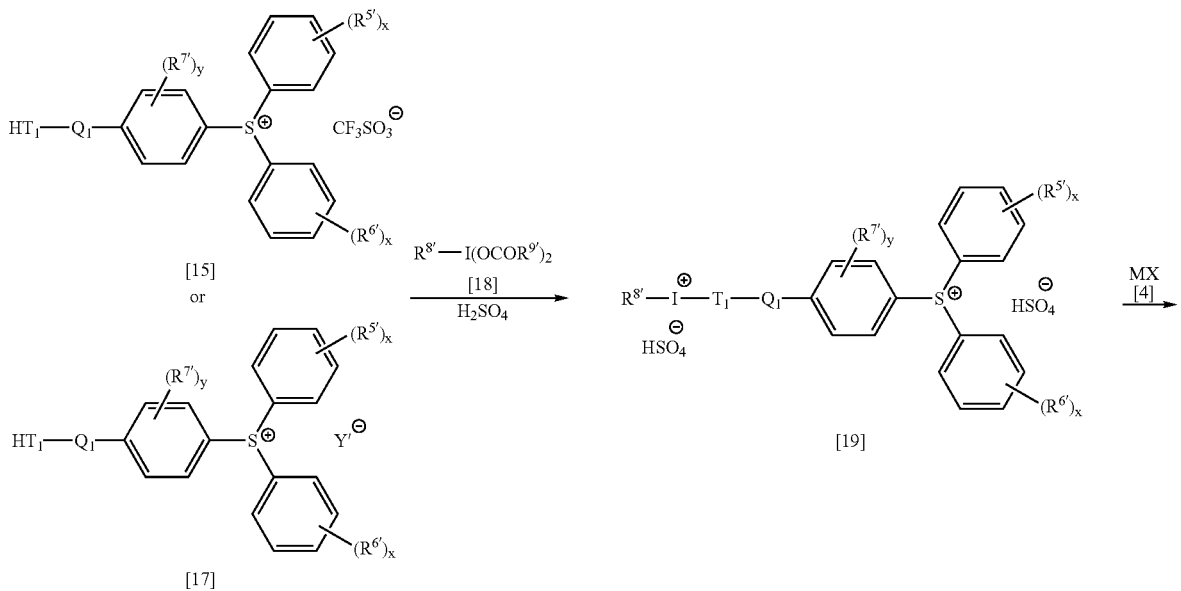

[G]

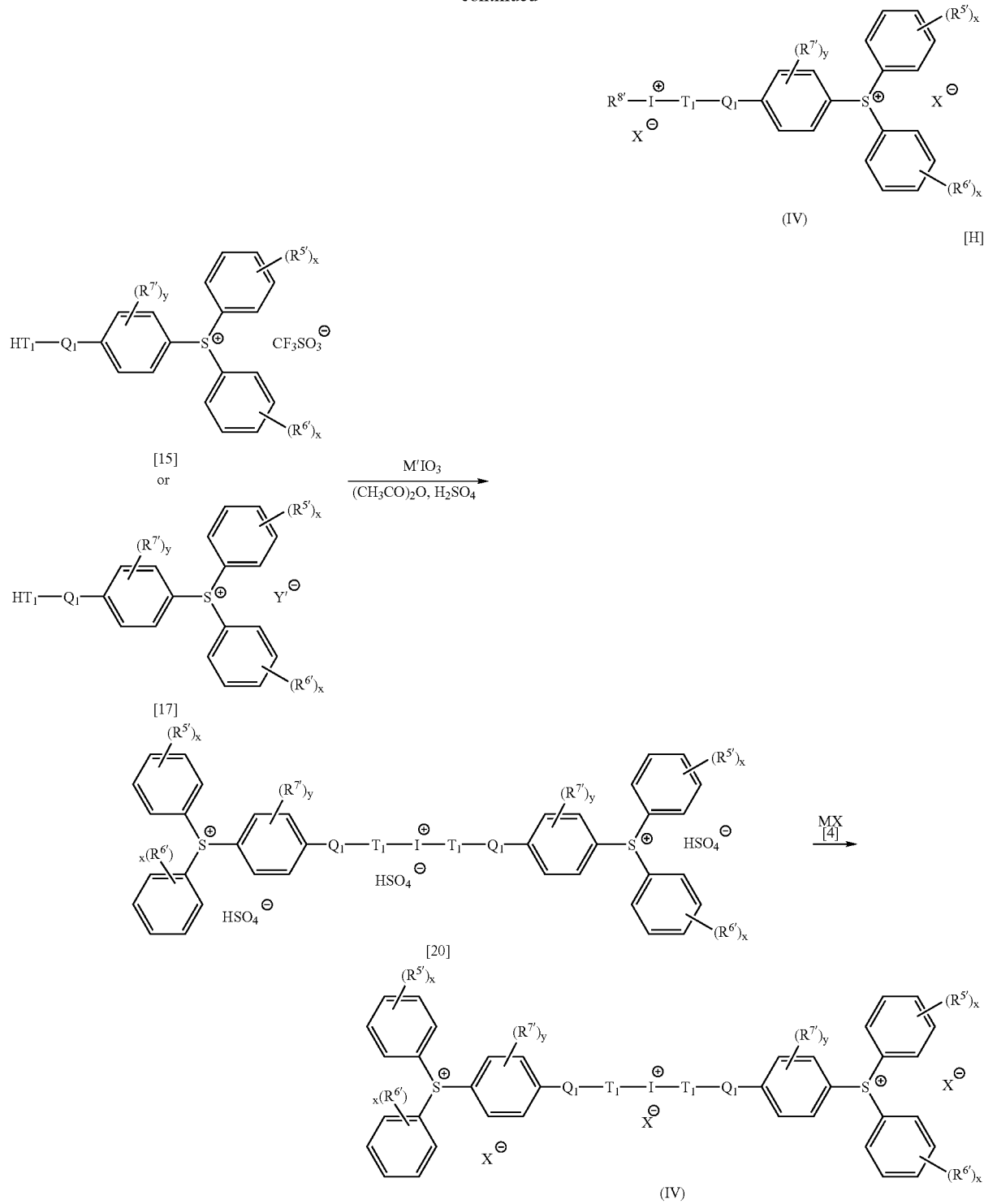

Further, the hybrid type onium salt of the present invention, shown by the Structure (IV) can be synthesized from the sulfonium salt shown by the above-described general formula [13], by the following methods [G], [H], and the like. Here, a method for manufacturing a hybrid type onium salt of the present invention, wherein a plurality of counterions thereof is the same, is shown (wherein $R^{9'}$ is a lower alkyl group or a lower haloalkyl group, Y' is a halogen atom, M is a metal atom, $X^-$ is a borate as described above, "n" is as described above, and $R^5$ to $R^8$ are independently halogen atoms, substituted or unsubstituted alkyl groups having 1 to 20 carbon atoms, substituted or unsubstituted haloalkyl groups having 1 to 20 carbon atoms, substituted or unsubstituted aryl groups having 6 or 10 carbon atoms in the aromatic rings, substituted or unsubstituted alkoxy groups having 1 to 20 carbon atoms, substituted or unsubstituted aryloxy groups having 6 or 10 carbon atoms in the aromatic rings, alkylthio groups having 1 to 20 carbon atoms in the alkyl groups, arylthio groups having 6 or 10 carbon atoms in the aromatic rings, or primary, secondary, or tertiary amino groups, all of which may be further substituted. Also, "x" is 0 or an integer of 1 to 5 and "y" is 0 or an integer of 1 to 4. $Q_1$, $T_1$ are the same as described above.

In the general formula [18], the lower haloalkyl group shown by $R^{9'}$ may be straight chained, branched or cyclic, and includes generally 1 to 6 carbon atoms (typically 1 to 3 carbon atoms) that is specifically exemplified by, for example, a methyl, ethyl, n-propyl, isopropyl, n-butyl, isobutyl, sec-butyl, tert-butyl, n-pentyl, isopentyl, sec-pentyl, tert-pentyl, neopentyl, 2-methylbutyl, 1-ethylpropyl, n-hexyl, isohexyl, sec-hexyl, tert-hexyl, neohexyl, 2-methylpentyl, 3-methylpentyl, 1,2-dimethylbutyl, 2,2-dimethylbutyl, 1-ethylbutyl, and 2-ethylbutyl groups. The lower haloalkyl group shown by $R^{9'}$ includes one or more of the hydrogen atoms being substituted by a halogen atom (such as a fluorine, chlorine, bromine, or iodine atom).

The metal atom shown by M' includes, for example, a lithium, sodium, potassium, rubidium, or cesium atom.

The compound shown by the general formula [18] may be a commercial product or a suitably synthesized using known reactants and reaction conditions.

In the method [G], a sulfonium salt compound shown by the general formula [15] or [17], synthesized by the above-described methods [D], [E] and [F], is dissolved in a carboxylic anhydride such as acetic anhydride and propionic anhydride or a mixed solvent consisting of carboxylic anhydrides and halogenated hydrocarbons such as methylene chloride, methylene bromide, 1,2-dichloroethane, and chloroform and aromatic hydrocarbons such as benzene, toluene and xylene, and a compound shown by the general formula [18] in an amount of 1 to 10 mole parts relative to 1 mole part of the compound is added thereto at −80 to 30° C., then sulfuric acid in an amount of 1 to 10 mole parts is further added dropwise thereto at −80 to 30° C. for 0.5 to 10 hours, followed by allowing a reaction to take place at −80 to 30° C. for 0.5 to 10 hours with stirring, thereby a desired compound shown by the general formula [19] is obtained. After completing the reaction, the reaction mixture is added to water and stirred. The resulting compound [19] is either removed by filtration or extracted with an organic solvent such as methylene chloride, 1,2-dichloroethane, ethyl acetate, butyl acetate, propylene glycol monomethyl ether acetate, methyl isobutyl ketone, and the desired polyonium borate of Structure (IV) is obtained using a borate exchange reaction in a solvent mixture of water and an alcohol such as methanol, ethanol, or propanol to provide the borate counterion.

In the method [H], a compound shown by the general formula [15] or [17] is dissolved in carboxylic anhydrides such as acetic anhydride and propionic anhydride or a mixed solvent consisting the carboxylic anhydrides and halogenated hydrocarbons such as methylene chloride, methylene bromide, 1,2-dichloroethane and chloroform and aromatic hydrocarbons such as benzene, toluene and xylene, and iodate salts ($M'IO_3$) such as lithium iodate, sodium iodate and potassium iodate in an amount of 0.4 to 0.6 mole parts relative to 1 mole part of said compound is added thereto at −70 to 30° C., then concentrated sulfuric acid in an amount of 1 to 10 mole parts or a mixed acid consisting of the concentrated sulfuric acid in 1 to 10 mole parts and carboxylic anhydrides such as acetic anhydride and propionic anhydride is added dropwise thereto at −70 to 30° C. for 0.5 to 10 hours, followed by allowing a reaction to take place at −70 to 30° C. for 0.5 to 10 hours with stirring. After completion of the reaction, the reaction solution is poured into ice water at 0 to 30° C., followed by extraction with halogenated hydrocarbons such as methylene chloride, methylene bromide, 1,2-dichloroethane and chloroform, and concentration, to obtain a desired compound shown by the general formula [20]. And the desired polyonium borate of Structure (IV) is obtained using a borate exchange reaction in a solvent mixture of water and an alcohol such as methanol, ethanol, or propanol to provide the borate counterion.

Representative synthetic methods are provided below just before the Examples.

Radiation-Sensitive Compositions

As noted above, the radiation-sensitive compositions described herein may have any utility wherever there is a need for a coating that is polymerizable or curable using suitable infrared radiation, and particularly where it is desired to remove unexposed regions of the coated and imaged composition. The radiation-sensitive compositions can be used to prepare an imageable layer in imageable elements such as printed circuit boards for integrated circuits, microoptical devices, paint compositions, molding compositions, color filters, photomasks, and particularly printed forms such as IR radiation-sensitive lithographic printing plate precursors and imaged printing plates that are defined in more detail below.

The free radically polymerizable component present in the radiation-sensitive composition and imageable layer contains one or more compounds having any polymerizable group that can be polymerized using free radical initiation. For example, the free radically polymerizable component can contain one or more free radical polymerizable monomers or oligomers having one or more addition polymerizable ethylenically unsaturated groups, crosslinkable ethylenically unsaturated groups, ring-opening polymerizable groups, azido groups, aryldiazonium salt groups, aryldiazosulfonate groups, or a combination thereof. Similarly, crosslinkable polymers having such free radically polymerizable groups can also be used.

Suitable ethylenically unsaturated compounds that can be polymerized or crosslinked include ethylenically unsaturated polymerizable monomers that have one or more of the polymerizable groups, including unsaturated esters of alcohols, such as acrylate and methacrylate esters of polyols. Oligomers and/or prepolymers, such as urethane acrylates and methacrylates, epoxide acrylates and methacrylates, polyester acrylates and methacrylates, polyether acrylates and methacrylates, and unsaturated polyester resins can also be used. In some embodiments, the free radically polymerizable component comprises carboxy groups.

Useful free radically polymerizable components include free-radical polymerizable monomers or oligomers that comprise addition polymerizable ethylenically unsaturated groups including multiple acrylate and methacrylate groups and combinations thereof, or free-radical crosslinkable polymers. Radically polymerizable compounds include those derived from urea urethane (meth)acrylates or urethane (meth)acrylates having multiple polymerizable groups. For example, a free radically polymerizable component can be prepared by reacting DESMODUR® N100 aliphatic polyisocyanate resin based on hexamethylene diisocyanate (Bayer Corp., Milford, Conn.) with hydroxyethyl acrylate and pentaerythritol triacrylate. Other free radically polymerizable compounds are available from Sartomer Company, Inc. such as Sartomer 399 ("SR 399", dipentaerythritol pentaacrylate), Sartomer 355 ("SR 355", di-trimethylolpropane tetraacrylate), Sartomer 295 ("SR 295", pentaerythritol tetraacrylate), and others that would be readily apparent to one skilled in the art.

Numerous other free radically polymerizable compounds are known to those skilled in the art and are described in considerable literature including *Photoreactive Polymers: The Science and Technology of Resists*, A Reiser, Wiley, New York, 1989, pp. 102-177, by B. M. Monroe in *Radiation Curing: Science and Technology*, S. P. Pappas, Ed., Plenum, New York, 1992, pp. 399-440, and in "Polymer Imaging" by A. B. Cohen and P. Walker, in *Imaging Processes and Material*, J. M. Sturge et al. (Eds.), Van Nostrand Reinhold, New York, 1989, pp. 226-262. For example, useful free radically polymerizable components are also described in EP 1,182,033A1 (noted above), beginning with paragraph [0170].

In some embodiments, the free radically polymerizable component comprises carboxy groups in an amount sufficient to provide an acid number greater than 0 mg KOH per grams of polymerizable component, and generally from 0 and up to and including 200 mg KOH per gram of the polymerizable component. For example, the acid number is from 0 and up to and including 100 mg KOH/gram of polymerizable component and more typically, it is from 0 and up to and including 60 mg KOH/gram of polymerizable component.

Free radically polymerizable compounds containing carboxy groups can be prepared in a number of ways. For example, oligomers containing carboxy groups can be prepared as described in the teaching of Col. 4 (line 42) to Col. 5 (line 19) and Col. 7 (line 14) to Col. 8 (line 45) of U.S. Pat. No. 4,228,232 (Rousseau). The carboxy groups can be added to the oligomers preferably after addition of the free radical polymerizable moieties by reaction of remaining hydroxy groups on the oligomer backbone with a compound having free carboxy groups (such as a dicarboxylic acid or anhydride). The resulting oligomers can be polymerized to provide a desired carboxy-substituted polymer.

Alternatively, a poly(urea urethane)acrylate or poly(urethane)-acrylate can be prepared from the reaction of a diisocyanate with a diol having free carboxy groups similarly to the preparation of allyl functional polyurethanes described in U.S. Pat. No. 5,919,600 (Huang et al.).

The free radically polymerizable component is present in the radiation-sensitive composition in an amount sufficient to render the composition insoluble in an aqueous developer after exposure to radiation. For example, the weight ratio of free radically polymerizable component to the polymeric binder (described below) is generally from about 5:95 to about 95:5, from about 10:90 to about 90:10, or from about 30:70 to about 70:30. The free radically polymerizable component can be present in an amount of at least 10 and up to and including 70%, typically at least 20 and up to and including 50%, based on the total solids in the radiation sensitive composition, or the total dry weight of the imageable layer.

The radiation-sensitive composition also includes an initiator composition that is capable of generating free radicals sufficient to initiate polymerization of the free radically polymerizable component upon exposure of the composition to imaging infrared radiation corresponding to the spectral range of at least 650 nm and up to and including 1500 nm and initiator compositions are used that are appropriate to that imaging range.

The initiator composition comprises one or more of the polyonium borates described above. These compounds may be used in combination with one or more co-initiators described below. The molar ratio of one or more polyonium borates to one or more co-initiators is 1:1 or more.

Useful co-initiators include metallocenes, polycarboxylic acids, haloalkyl triazines, thiols, monovalent onium borates (that is, compounds having an onium cation with a single positive charge), and photooxidants containing a heterocyclic nitrogen that is substituted by an alkoxy or acyloxy group, as described in U.S. Pat. No. 5,942,372 (West et al.) and tetraaryl borate and triarylalkyl borates.

Thus, one combination of compounds in the initiator composition includes one or more polyonium borates with a metallocene (for example a titanocene or ferrocene) as described for example in U.S. Pat. No. 6,936,384 (noted above).

Alternatively, the polyonium borates may be used in combination with heterocyclic mercapto compounds including mercaptotriazoles, mercaptobenzimidazoles, mercaptobenzoxazoles, mercaptobenzothiazoles, mercaptobenzoxadiazoles, mercaptotetrazoles, such as those described for example in U.S. Pat. No. 6,884,568 (Timpe et al.) in amounts of at least 0.5 and up to and including 10 weight % based on the total solids of the radiation-sensitive composition. Useful mercaptotriazoles include 3-mercapto-1,2,4-triazole, 4-methyl-3-mercapto-1,2,4-triazole, 5-mercapto-1-phenyl-1,2,4-triazole, 4-amino-3-mercapto-1,2,4,-triazole, 3-mercapto-1,5-diphenyl-1,2,4-triazole, and 5-(p-aminophenyl)-3-mercapto-1,2,4-triazole.

The free radical generating compounds (that is, the polyonium borates) in the initiator composition are generally present in the radiation-sensitive composition in an amount of at least 0.1% and up to and including 20%, and typically at least 3 and up to and including about 15%, based on composition total solids or total dry weight of the imageable layer. The optimum amount of the various initiator components (initiator and optional co-initiator) may differ for various compounds and the sensitivity of the radiation-sensitive composition that is desired and would be readily apparent to one skilled in the art.

Any of a variety of polymeric binders can be used in the radiation-sensitive composition, including those known in the art for use in negative-working radiation-sensitive compositions. The polymeric binders generally have a molecular weight of at least 2,000 and up to and including 1,000,000, at least 10,000 and up to and including 200,000, or at least 10,000 and up to and including 100,000. The acid value (mg KOH/g) of the polymeric binder is generally from about 0 and up to and including 400, at least 0 and up to and including 200, or at least 0 and up to and including 130, as determined using known methods.

Some binders are water-insoluble but soluble in conventional alkaline developers. Examples of such polymeric binders include but are not limited to, (meth)acrylic acid ester resins, polyvinyl acetals, phenolic resin, polymers derived from styrene, N-substituted cyclic imides or maleic anhydrides, such as those described in EP 1,182,033 (noted above) and U.S. Pat. No. 6,309,792 (noted above), U.S. Pat. No. 6,352,812 (Shimazu et al.), U.S. Pat. No. 6,569,603 (noted above), and U.S. Pat. No. 6,893,797 (noted above), all incorporated herein by reference with respect to the polymeric binders. Also useful are the vinyl carbazole polymers having pendant N-carbazole moieties as described in copending and commonly assigned U.S. Ser. No. 11/356,518 (filed Feb. 17, 2006 by Tao et al.) and the polymers having pendant vinyl groups as described in copending and commonly assigned 11/349,376 (filed Feb. 7, 2006 by Tao et al.), both of which are incorporated herein by reference.

Other useful polymeric binders are dispersible, developable, or soluble in water or water/solvent mixtures such as fountain solutions. Such polymeric binders include polymeric emulsions, dispersions, or graft polymers having pendant poly(alkyleneoxide) side chains that can render the imageable elements as "on-press" developable. Such polymeric binders are described for example in U.S. Pat. Nos. 6,582,882 and 6,899,994 (both noted above). In some instances, these polymeric binders are present in the imageable layer as discrete particles.

Some polymeric binders (at least 60 weight % of total dry polymeric binders) in the radiation-sensitive composition (and imageable elements described below) are those having poly(alkylene glycol) side chains directly or indirectly linked to the polymeric backbone. Typically, at least 5 weight % and up to and including 100 weight % of the total polymeric binders are composed of one or more of such polymeric binders.

Many of such polymeric binders are dispersible, developable, or soluble in water or water/solvent mixtures such as fountain solutions or mixtures of fountain solutions and lithographic printing inks. Such polymeric binders include polymeric emulsions, dispersions, or polymers having the pendant poly(alkylene glycol) side chains that can render the imageable elements as "on-press" developable. Such polymeric binders are described for example in U.S. Pat. Nos. 6,582,882 and 6,899,994 (both noted above). In some instances, these polymeric binders are present in the imageable layer at least partially and alternatively entirely, as discrete particles.

Other useful polymeric binders have hydrophobic backbones and comprise both of the following a) and b) recurring units, or the b) recurring units alone:

a) recurring units having pendant cyano groups attached directly to the hydrophobic backbone, and b) recurring units having pendant groups comprising poly(alkylene glycol) side chains.

These polymeric binders comprise poly(alkylene glycol) and cyano side chains. These polymers can be graft copolymers having a main chain polymer and poly(alkylene glycol) pendant side chains. Other polymers are block copolymers having blocks or segments of (alkylene glycol)-containing recurring units and non(alkylene glycol)-containing recurring units. Both graft and block copolymers can additionally have pendant cyano groups attached directly to the hydrophobic backbone. The alkylene glycol side chains generally comprise at least 10 constitutional alkylene glycol units and up to and including 150 of such units, at least 10 and up to and including 100 of such units, at least 10 and up to and including 50 of such alkylene glycol units, or at least 15 and up to and including 50 of such alkylene glycol units. The constitutional alkylene glycol units can be the same or different in an individual side chain and are generally $C_1$ to $C_6$ alkylene glycol groups, and more typically $C_1$ to $C_3$ alkylene glycol groups. The alkylene portions can be linear or branched or substituted versions thereof. Poly(ethylene glycol) and poly(propylene glycol) side chains are useful.

As noted above, in some embodiments, the polymeric binders comprise recurring units comprising the poly(alkylene glycol) side chains as well as recurring units having pendant cyano groups attached directly to the hydrophobic backbone. By way of example only, such recurring units can comprise pendant groups comprising cyano or cyano-substituted or cyano-terminated alkylene groups. Recurring units can also be derived from ethylenically unsaturated polymerizable monomers such as acrylonitrile, methacrylonitrile, methyl cyanoacrylate, ethyl cyanoacrylate, or a combination thereof. However, cyano groups can be introduced into the polymer by other conventional means. Examples of such cyano-containing polymeric binders are described for example in U.S. Patent Application Publication 2005/003285 (Hayashi et al.).

By way of example, polymeric binders that are useful in the IR-sensitive compositions and imageable elements can be formed by polymerization of a combination or mixture of suitable ethylenically unsaturated polymerizable monomers or macromers, such as:

A) acrylonitrile, methacrylonitrile, or a combination thereof,

B) poly(alkylene glycol) esters of acrylic acid or methacrylic acid, such as poly(ethylene glycol) methyl ether acrylate, poly(ethylene glycol) methyl ester methacrylate, or a combination thereof, and C) optionally, monomers such as acrylic acid, methacrylic acid, styrene, hydroxystyrene, acrylate esters, vinyl carbazole, methacrylate esters, acrylamide, N-phenyl maleimide, carboxyphenyl methacrylamide, allyl methacrylate, carboxyphenyl maleimide, 2-acrylamido-2-methyl-1-propane sulfonic acid, methacrylamide, or a combination of such monomers.

The amount of the poly(alkylene glycol) side chains in such polymeric binders is at least 0.5 and up to and including 60 weight %, at least 2 and up to and including 50 weight %, at least 5 and up to and including 40 weight %, or at least 5 and up to and including 20 weight %, based on the total polymeric binder weight. The amount of poly(alkylene glycol) segments in block copolymers is generally at least 5 and up to and including 60 weight %, at least 10 and up to and including 50 weight %, or at least 10 and up to and including 30 weight %.

Where the polymeric binders comprise pendant cyano groups, the amount of such cyano groups is at least 5 and up to and including 99.5 weight %, at least 10 and up to and including 80 weight %, or at least 25 and up to and including 60 weight %, based on the total polymeric binder weight.

The polymeric binders comprising (alkylene glycol) side chains are generally present in an amount of at least 10 and up to and including 90%, or at least 20 and up to and including 80%, based on the total solids content of the radiation-sensitive composition or the dry weight of the imageable layer prepared therefrom.

In some embodiments, it may be useful to include a "secondary" polymeric binder in combination with the polymeric binders described above. Such secondary polymeric binders include acrylic-urethane hybrid polymers that are commercially available in dispersions from Air Products and Chemicals, Inc. (Allentown, Pa.) under the tradename Hybridur, for example, the Hybridur 540, 560, 570, 580, 870, and 878 acrylic-urethane hybrid dispersions. Other secondary polymeric binders are water-insoluble but soluble in conventional alkaline developers. Examples of such polymeric binders include but are not limited to, (meth)acrylic acid and acid ester resins [such as (meth)acrylates], polyvinyl acetals, phenolic resin, polymers derived from styrene, N-substituted cyclic imides or maleic anhydrides, such as those described in EP 1,182,033 (noted above) and U.S. Pat. Nos. 6,309,792 (noted above), U.S. Pat. No. 6,352,812 (Shimazu et al.), U.S. Pat. No. 6,569,603 (noted above), and U.S. Pat. No. 6,893,797 (noted above). Also useful are the vinyl carbazole polymers described in copending and commonly assigned U.S. Ser. No. 11/356,518 (filed Feb. 17, 2006 by Tao et al.) and the polymers having pendant vinyl groups as described in copending and commonly assigned U.S. Ser. No. 11/349,376 (filed Feb. 7, 2006 by Tao et al.), both of which are incorporated herein by reference. The secondary polymeric binder may be present in the radiation-sensitive composition in an amount of from about 5 to about 40 weight % based on the total solids content of the composition, or the dry coated weight of the imageable layer.

The radiation-sensitive composition generally includes one or more radiation absorbing compounds, or sensitizers, that absorb imaging radiation, or sensitize the composition to imaging radiation having a $\lambda_{max}$ in the IR region of the electromagnetic spectrum, that is, at least 700 nm and up to and including 1500 nm. Some sensitizers can be used at any wavelength, but most sensitizers are optimally useful within certain wavelength ranges. The radiation-sensitive compositions can comprise an infrared radiation absorbing compound ("IR absorbing compounds") that absorbs radiation of at least 700 nm and up to and including 1500 nm and typically of at least 750 nm and up to and including about 1200 nm. For imageable elements designed for on-press development, it may be useful for such IR absorbing compounds to be used in combination with onium salts to enhance polymerization of the polymerizable component and to produce a more durable printing plate.

Useful IR-sensitive radiation absorbing compounds include carbon blacks and other IR-absorbing pigments and various IR-sensitive dyes ("IR dyes"). Examples of suitable IR dyes include but are not limited to, azo dyes, squarilium dyes, croconate dyes, triarylamine dyes, thioazolium dyes, indolium dyes, oxonol dyes, oxaxolium dyes, cyanine dyes, merocyanine dyes, phthalocyanine dyes, indocyanine dyes, indotricarbocyanine dyes, oxatricarbocyanine dyes, thiocyanine dyes, thiatricarbocyanine dyes, merocyanine dyes, cryptocyanine dyes, naphthalocyanine dyes, polyaniline dyes, polypyrrole dyes, polythiophene dyes, chalcogenopyryloarylidene and bi(chalcogenopyrylo) polymethine dyes, oxyindolizine dyes, pyrylium dyes, pyrazoline azo dyes, oxazine dyes, naphthoquinone dyes, anthraquinone dyes, quinoneimine dyes, methine dyes, arylmethine dyes, squarine dyes, oxazole dyes, croconine dyes, porphyrin dyes, and any substituted or ionic form of the preceding dye classes. Suitable dyes are also described in U.S. Pat. No. 5,208,135 (Patel et al.) that is incorporated herein by reference.

A general description of one class of suitable cyanine dyes is shown by the formula in paragraph [0026] of WO 2004/101280 (Munnelly et al.), incorporated herein by reference, and a useful IR absorbing compounds is identified below with the Examples.

In addition to low molecular weight. IR-absorbing dyes, IR dye moieties bonded to polymers can be used as well. Moreover, IR dye cations can be used as well, that is, the cation is the IR absorbing portion of the dye salt that ionically interacts with a polymer comprising carboxy, sulfo, phospho, or phosphono groups in the side chains.

Near infrared absorbing cyanine dyes are also useful and are described for example in U.S. Pat. No. 6,309,792 (Hauck et al.), U.S. Ser. No. 6,264,920 (Achilefu et al.), U.S. Ser. No. 6,153,356 (Urano et al.), U.S. Ser. No. 5,496,903 (Watanate et al.). Suitable dyes may be formed using conventional methods and starting materials or obtained from various commercial sources including American Dye Source (Baie D'Urfe, Quebec, Canada) and FEW Chemicals (Germany). Other useful dyes for near infrared diode laser beams are described, for example, in U.S. Pat. No. 4,973,572 (DeBoer).

Useful IR absorbing compounds include carbon blacks including carbon blacks that are surface-functionalized with solubilizing groups are well known in the art. Carbon blacks that are grafted to hydrophilic, nonionic polymers, such as FX-GE-003 (manufactured by Nippon Shokubai), or which are surface-functionalized with anionic groups, such as CAB-O-JET® 200 or CAB-O-JET® 300 (manufactured by the Cabot Corporation) are also useful.

Some useful infrared radiation absorbing dyes have a tetraaryl pentadiene chromophore. Such chromophore generally includes a pentadiene linking group having 5 carbon atoms in the chain, to which are attached two substituted or unsubstituted aryl groups at each end of the linking group. The pentadiene linking group can also be substituted with one or more substituents in place of the hydrogen atoms, or two or more hydrogen atoms can be replaced with atoms to form a ring in the linking group as long as there are alternative carbon-carbon single bonds and carbon-carbon double bonds in the chain.

For example, representative useful IR-sensitive dyes of this type can be defined by the following Structure DYE-I:

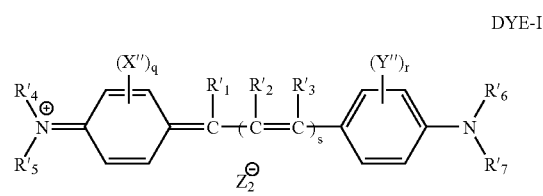

DYE-I wherein $R_1'$, $R_2'$, and $R_3'$ each independently represents hydrogen, or a halo, cyano, substituted or unsubstituted alkoxy (having 1 to 8 carbon atoms, both linear and branched alkoxy groups), substituted or unsubstituted aryloxy (having 6 to 10 carbon atoms in the carbocyclic ring), substituted or unsubstituted acyloxy (having 2 to 6 carbon atoms), carbamoyl, substituted or unsubstituted acyl, substituted or unsubstituted acylamido, substituted or unsubstituted alkylamino (having at least one carbon atom), substituted or unsubstituted carbocyclic aryl groups (having 6 to 10 carbon atoms in the aromatic ring, such as phenyl and naphthyl groups), substituted or unsubstituted alkyl groups (having 1 to 8 carbon atoms, both linear and branched isomers), substituted or unsubstituted arylamino, or substituted or unsubstituted heteroaryl (having at least 5 carbon and heteroatoms in the ring) group. Alternatively, any two of $R_1'$, $R_2'$, and $R_3'$ groups may be joined together or with an adjacent aromatic ring to complete a 5- to 7-membered substituted or unsubstituted carbocyclic or heterocyclic ring.

For example, $R_1'$, $R_2'$, $R_3'$ are independently hydrogen, a substituted or unsubstituted carbocyclic aryl group, and a substituted or unsubstituted heteroaryl group.

$R_4'$, $R_5'$, $R_6'$, and $R_7'$ each independently represents hydrogen, a substituted or unsubstituted alkyl group (having 1 to 10 carbon atoms), a substituted or unsubstituted cycloalkyl group (having from 4 to 6 carbon atoms in the ring), a substituted or unsubstituted aryl group (having at least 6 carbon atoms in the ring), or a substituted or unsubstituted heteroaryl group (having 5 to 10 carbon and heteroatoms in the ring).

Alternatively, $R_4'$ and $R_5'$ or $R_6'$ and $R_7'$ can be joined together to form a substituted or unsubstituted 5- to 9-membered heterocyclic ring, or $R_4'$, $R_5'$, $R_6'$, or $R_7'$ can be joined to the carbon atom of the adjacent aromatic ring at a position ortho to the position of attachment of the anilino nitrogen to form, along with the nitrogen to which they are attached, a substituted or unsubstituted 5- or 6-membered heterocyclic ring.

For example, $R_4'$, $R_5'$, $R_6'$, and $R_7'$ are independently a substituted or unsubstituted alkyl group, a substituted or unsubstituted cycloalkyl group, a substituted or unsubstituted aryl group, or $R_4'$ and $R_5'$ or $R_6'$ and $R_7'$ can be joined together to form a substituted or unsubstituted 5- to 7-membered heterocyclic ring. Also, they can be independently substituted or unsubstituted alkyl groups of 1 to 8 carbon atoms, substituted or unsubstituted phenyl groups, or $R_4'$ and $R_5'$ or $R_6'$ and $R_7'$ can be joined together to form a substituted or unsubstituted 5- to 7-membered heteroaryl group.

In the DYE I structure, s is 2, $Z_2$ is a monovalent anion, X" and Y" are each independently $R_1'$ or the atoms necessary to complete a substituted or unsubstituted 5- to 7-membered fused carbocyclic or heterocyclic ring, and q and r are independently integers from 1 to 4.

For example, X" and Y" are independently hydrogen or the carbon and heteroatoms needed to provide a fused aryl or heteroaryl ring.

Further details of such bis(aminoaryl)pentadiene IR dyes are provided, including representative IR dyes identified as DYE 1 through DYE 17, DYE 19, and DYE 20, in U.S. Pat. No. 6,623,908 (Zheng et al.) that is incorporated herein by reference for this IR dye description and representative compounds.

In addition, representative IR-sensitive dyes can also be represented by the following Structure DYE-II:

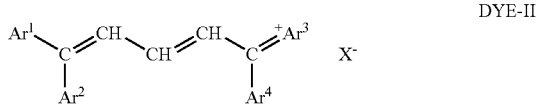

DYE-II wherein $Ar^1$ through $Ar^4$ are the same or different substituted or unsubstituted aryl groups having at least carbon atoms in the aromatic ring (such as phenyl, naphthyl, and anthryl, or other aromatic fused ring systems) wherein 1 to 3 of the aryl groups are substituted with the same or different tertiary amino group (such as in the 4-position of a phenyl group). Typically two of the aryl groups are substituted with the same or different tertiary amino group, and usually at different ends of the polymethine chain (that is, molecule). For example, $Ar^1$ or $Ar^2$ and $Ar^3$ or $Ar^4$ bear the tertiary amine groups. Representative amino groups include but are not limited to those substituted with substituted or unsubstituted alkyl groups having up to 10 carbon atoms or aryl groups such as dialkylamino groups (such as dimethylamino and diethylamino), diarylamino groups (such as diphenylamino), alkylarylamino groups (such as N-methylanilino), and heterocyclic groups such as pyrrolidino, morpholino, and piperidino groups. The tertiary amino group can form part of a fused ring such that one or more of $Ar^1$ through $Ar^4$ can represent a julolidine group.

Besides the noted tertiary groups noted above, the aryl groups can be substituted with one or more substituted or unsubstituted alkyl groups having 1 to 10 carbon atoms, halo atoms (such as chloro or bromo), hydroxyl groups, thioether groups, and substituted or unsubstituted alkoxy groups having 1 to 10 carbon atoms. Substituents that contribute electron density to the conjugated system are useful. While they are not specifically shown in Structure (DYE-II), substituents or fused rings may also exist on (or as part of) the conjugated chain connecting the aryl groups.

In Structure (DYE-II), X⁻ is a suitable counterion that may be derived from a strong acid, and include such anions as $ClO_4^-$, $BF_4^-$, $CF_3SO_3^-$, $PF_6^-$, $AsF_6^-$, $SbF_6^-$, and perfluoroethylcyclohexylsulfonate. Other cations include boron-containing counterions (borates), methylbenzenesulfonic acid, benzenesulfonic acid, methanesulfonic acid, p-hydroxybenzenesulfonic acid, p-chlorobenzenesulfonic acid, and halides.

Two representative IR dyes defined by Structure (DYE-II) are defined as D1 and D2 in WO 98/07574 (Patel et al.) that is incorporated by reference for these dyes and the synthetic method described therein.

Representative useful IR-sensitive dyes of this type are represented by the following Structure (DYE-III):

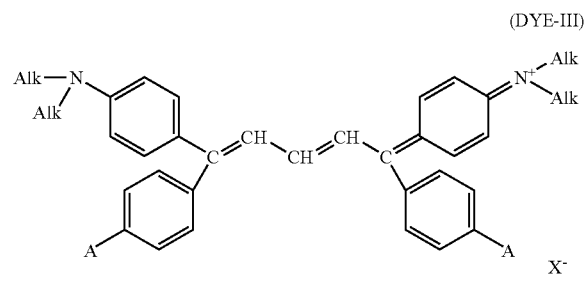

(DYE-III)

wherein "Alk" represents the same or different substituted or unsubstituted alkyl groups having 1 to 7 carbon atoms (such as substituted or unsubstituted methyl, ethyl, iso-propyl, t-butyl, n-hexyl, and benzyl), and "A" represents hydrogen or the same or different substituted or unsubstituted lower alkyl group having 1 to 3 carbon atoms (such as methyl, ethyl, n-propyl, and iso-propyl), or the same or different dialkylamino groups similar to those defined above for Structure (DYE-2), wherein such groups have the same or different alkyl groups. X⁻ is a suitable counterion as defined above for Structure (DYE-II).

Some IR dyes include a borate anion, such as a tetrasubstituted borate anion, which substituents can be the same or different alkyl (having 1 to 20 carbon atoms) or aryl groups (phenyl or naphthyl groups), which groups can be further substituted if desired. Particularly useful boron-containing counterions of this type include alkyltriarylborates, dialkyldiarylborates, and tetraarylborates. Examples of these boron-containing counterions are described for example, in EP 438,123A2 (Murofushi et al.).

Representative useful dyes of this type are described as Dyes 2, 3-A, 3-B, 3-C, 12, and 22 described in EP 438,123A2 (noted above)

Useful infrared radiation absorbing dyes can be obtained from a number of commercial sources including Showa Denko (Japan) or they can be prepared using known starting materials and procedures. For example, IR dyes represented by Structure (DYE-I) can be prepared using the synthetic method illustrated in U.S. Pat. No. 6,623,908 (noted above) just before the examples, and IR dyes represented by Structures (DYE-II) and (DYE-III) can be prepared using the synthetic procedure described on page 10 (lines 11-14) of WO 98/07574 (noted above).

The radiation absorbing compound (or sensitizer) can be present in the radiation-sensitive composition in an amount generally of at least 0.1% and up to and including 30% and typically at least 2 and up to and including 15%, based on total solids in the composition, that also corresponds to the total dry weight of the imageable layer. The particular amount needed for this purpose would be readily apparent to one skilled in the art, depending upon the specific compound used.

The radiation-sensitive composition can also comprise one or more nonionic phosphate (meth)acrylates, each of which has a molecular weight generally greater than 250 and typically at least 300 and up to and including 1000. By "nonionic" we mean that the phosphate (meth)acrylates not only are neutral in charge but they have no internal positive or negative charges. Thus, they are not internal salts or salts formed with an external cation or anion. Moreover, by "phosphate (meth)acrylate" we mean to include both "phosphate acrylates" and "phosphate methacrylates" and other derivatives having substituents on the vinyl group in the acrylate moiety.

Each phosphate moiety may be connected to a (meth) acrylate moiety by an alkyleneoxy chain, that is a -(alkylene-O)$_m$— chain composed of at least one alkyleneoxy unit, in which the alkylene moiety has 2 to 6 carbon atoms and can be either linear or branched and m is 1 to 10. For example, the alkyleneoxy chain can comprise ethyleneoxy units, and m is from 2 to 8 or m is from 3 to 6. The alkyleneoxy chains in a specific compound can be the same or different in length and have the same or different alkylene group.

Representative nonionic phosphate (meth)acrylates useful in this invention can be represented by the following Structure (V):

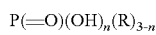

wherein the R groups are independently the same or different groups represented by the following Structure (VI):

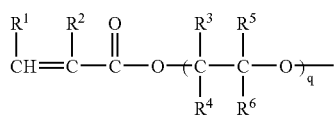

wherein $R^1$ and $R^2$ are independently hydrogen, or a halo group (such as fluoro, chloro, bromo, or iodo) or a substituted or unsubstituted alkyl group having 1 to 4 carbon atoms (such as methyl, chloromethyl, ethyl, isopropyl, n-butyl, and t-butyl). For example, $R^1$ and $R^2$ are independently hydrogen, methyl, or chloro, and typically, they are independently hydrogen or methyl.

$R^3$ through $R^6$ are independently hydrogen or a substituted or unsubstituted alkyl group having 1 to 5 carbon atoms (such as methyl, chloromethyl, hydroxymethyl, ethyl, iso-propyl, n-butyl, t-butyl, and n-pentyl). For example, $R^3$ through $R^6$ are independently hydrogen or substituted or unsubstituted methyl or ethyl groups, and typically, they are independently hydrogen or unsubstituted methyl groups.

Also, in Structure V, n is 1 or 2.

In Structure VI, q is 1 to 10, or from 2 to 8, for example from 3 to 6.

Representative nonionic phosphate (meth)acrylates useful in this invention include but are not limited to, ethylene glycol methacrylate phosphate (available from Aldrich Chemical Co.), a phosphate of 2-hydroxyethyl methacrylate that is available as Kayamer PM-2 from Nippon Kayaku (Japan) that is shown below, a phosphate of caprolactone modified 2-hydroxyethyl methacrylate that is available as Kayamer PM-21 (Nippon Kayaku, Japan) that is also shown below, and an ethylene glycol methacrylate phosphate with 4-5 ethoxy groups that is available as Phosmer PE from Uni-Chemical Co., Ltd. (Japan) that is also shown below. Other useful nonionic phosphate (meth)acrylates are shown below.

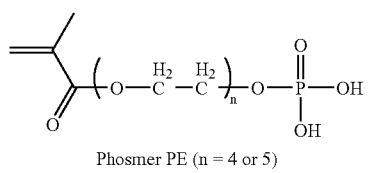

Phosmer PE (n = 4 or 5)

-continued

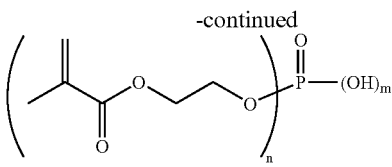

Kayamer PM-2 (m = 1 or 2, n = 3 - m)

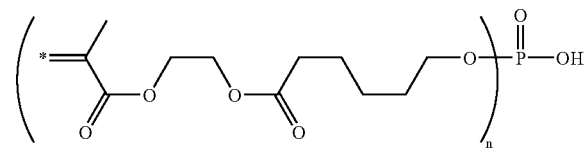

Kayamer PM-21 (n = 2)

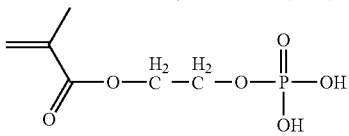

Phosmer M

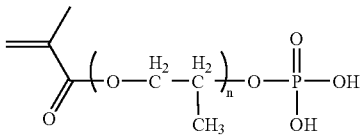

Phosmer PP (n = 5 or 6)

The nonionic phosphate (meth)acrylate may be present in the radiation-sensitive composition in an amount of at least 0.6 and up to and including 20% and typically at least 0.9 and up to and including 10%, by weight of the total solids. In the dry imageable layers of the imageable elements, the nonionic phosphate (meth)acrylate may be present in an amount of at least 8 mg/m$^2$ and up to and including 300 mg/m$^2$ and typically at least 10 and up to and including about 150 mg/m$^2$.

The radiation-sensitive composition can also include a "primary additive" that is a poly(alkylene glycol) or an ether or ester thereof that has a molecular weight of at least 200 and up to and including 4000. This primary additive is present in an amount of at least 2 and up to and including 50 weight %, based on the total solids content of the composition, or the total dry weight of the imageable layer.

Particularly useful primary additives include, but are not limited to, one or more of polyethylene glycol, polypropylene glycol, polyethylene glycol methyl ether, polyethylene glycol dimethyl ether, polyethylene glycol monoethyl ether, polyethylene glycol diacrylate, ethoxylated bisphenol A di(meth) acrylate, and polyethylene glycol mono methacrylate. Also useful are SR9036 (ethoxylated (30) bisphenol A dimethacrylate), CD9038 (ethoxylated (30) bisphenol A diacrylate), and SR494 (ethoxylated (5) pentaerythritol tetraacrylate), and similar compounds all of which that can be obtained from Sartomer Company, Inc. In some embodiments, the primary additive may be "non-reactive" meaning that it does not contain polymerizable vinyl groups.

The radiation-sensitive composition can also include a "secondary additive" that is a poly(vinyl alcohol), a poly (vinyl pyrrolidone), poly(vinyl imidazole), or polyester in an amount of up to and including 20 weight % based on the total solids content of the composition, or the total dry weight of the imageable layer.

The radiation-sensitive composition can also include a variety of optional compounds including but not limited to, dispersing agents, humectants, biocides, plasticizers, surfactants for coatability or other properties, viscosity builders, dyes or colorants to allow visualization of the written image (such as crystal violet, methyl violet, ethyl violet, Victoria blue, malachite green, and brilliant green), pH adjusters, drying agents, defoamers, preservatives, antioxidants, development aids, rheology modifiers or combinations thereof, or any other addenda commonly used in the lithographic art, in conventional amounts. Useful viscosity builders include hydroxypropyl cellulose, hydroxyethyl cellulose, carboxymethyl cellulose, and poly(vinyl pyrrolidones).

As examples of useful antioxidants, which may act to extend shelf-life of the imageable element, are compounds that prevent oxidation of the polymeric binder(s) or infrared radiation absorbing dyes including but not limited to, phosphorus-containing antioxidants, sulfur-based antioxidants, amine-containing antioxidants, and phenol-containing antioxidants. Examples of such antioxidants and useful amounts are described in [0051]-[0060] of U.S. Patent Application Publication 2003/0031951 (Aburano), which antioxidant disclosure is incorporated herein by reference.

Imageable Elements

The imageable elements are formed by suitable application of a radiation-sensitive composition as described above to a suitable substrate to form an imageable layer. This substrate can be treated or coated in various ways as described below prior to application of the radiation-sensitive composition. There may be only a single imageable layer comprising the radiation-sensitive composition. If the substrate has been treated to provide an "interlayer" for improved adhesion or hydrophilicity, the applied radiation-sensitive composition is generally considered the "top" or outermost layer. These interlayers, however, are not considered "imageable layers". Typically, an overcoat (such as an oxygen impermeable topcoat) is applied to the imageable layer(s) as described in WO 99/06890 (Pappas et al.). Such overcoat layers can comprise one or more water-soluble polymers such as poly(vinyl alcohol), poly(vinyl pyrrolidone), poly(ethyleneimine), and poly(vinyl imidazole) and generally have a dry coating weight of at least 0.1 and up to and including 4 $g/m^2$.

The substrate generally has a hydrophilic surface, or at least a surface that is more hydrophilic than the applied radiation-sensitive composition on the imaging side. The substrate comprises a support that can be composed of any material that is conventionally used to prepare imageable elements such as lithographic printing plates. It is usually in the form of a sheet, film, or foil and is strong, stable, and flexible and resistant to dimensional change under conditions of use so that color records will register a full-color image. Typically, the support can be any self-supporting material including polymeric films (such as polyester, polyethylene, polycarbonate, cellulose ester polymer, and polystyrene films), glass, ceramics, metal sheets or foils, or stiff papers (including resin-coated and metallized papers), or a lamination of any of these materials (such as a lamination of an aluminum foil onto a polyester film). Metal supports include sheets or foils of aluminum, copper, zinc, titanium, and alloys thereof.

Polymeric film supports may be modified on one or both flat surfaces with a "subbing" layer to enhance hydrophilicity, or paper supports may be similarly coated to enhance planarity. Examples of subbing layer materials include but are not limited to, alkoxysilanes, amino-propyltriethoxysilanes, glycidioxypropyl-triethoxysilanes, and epoxy functional polymers, as well as conventional hydrophilic subbing materials used in silver halide photographic films (such as gelatin and other naturally occurring and synthetic hydrophilic colloids and vinyl polymers including vinylidene chloride copolymers).

One useful substrate is composed of an aluminum support that may be treated using techniques known in the art, including roughening of some type by physical (mechanical) graining, electrochemical graining, or chemical graining, usually followed by acid anodizing. The aluminum support can be roughened by physical or electrochemical graining and then anodized using phosphoric or sulfuric acid and conventional procedures. A useful substrate is an electrochemically grained and sulfuric acid anodized aluminum support.

An interlayer may be formed on the aluminum support by treating it with, for example, a silicate, dextrine, calcium zirconium fluoride, hexafluorosilicic acid, poly(vinyl phosphonic acid)(PVPA), vinyl phosphonic acid copolymer, poly(acrylic acid), acrylic acid copolymer, or an alkali salt of a condensed aryl sulfonic acid as described in GB 2,098,627 and Japanese Kokai 57-195697A (both Herting et al.). Still further, the aluminum support may be treated with a phosphate solution that may further contain an inorganic fluoride (PF). The aluminum support can be electrochemically-grained, sulfuric acid-anodized, and treated with PVPA or PF using known procedures to improve surface hydrophilicity.

The thickness of the substrate can be varied but should be sufficient to sustain the wear from printing and thin enough to wrap around a printing form. Useful embodiments include a treated aluminum foil having a thickness of at least 100 μm and up to and including 600 μm.

The backside (non-imaging side) of the substrate may be coated with antistatic agents and/or slipping layers or a matte layer to improve handling and "feel" of the imageable element.

The substrate can also be a cylindrical surface having the radiation-sensitive composition applied thereon, and thus be an integral part of the printing press. The use of such imaging cylinders is described for example in U.S. Pat. No. 5,713,287 (Gelbart).

The radiation-sensitive composition can be applied to the substrate as a solution or dispersion in a coating liquid using any suitable equipment and procedure, such as spin coating, knife coating, gravure coating, die coating, slot coating, bar coating, wire rod coating, roller coating, or extrusion hopper coating. The composition can also be applied by spraying onto a suitable support (such as an on-press printing cylinder). Typically, the radiation-sensitive composition is applied as the outermost layer.

Illustrative of such manufacturing methods is mixing the radically polymerizable component, initiator composition, radiation absorbing compound, polymeric binder, primary additive, and any other components of the radiation-sensitive composition in a suitable organic solvent [such as methyl ethyl ketone (2-butanone), methanol, ethanol, 1-methoxy-2-propanol, iso-propyl alcohol, acetone, γ-butyrolactone, n-propanol, tetrahydrofuran, and others readily known in the art, as well as mixtures thereof], applying the resulting solution to a substrate, and removing the solvent(s) by evaporation under suitable drying conditions. Some coating solvents and representative imageable layer formulations are described in the Examples below. After proper drying, the coating weight of the imageable layer is generally at least 0.1 and up to and including 5 $g/m^2$ or at least 0.5 and up to and including 3.5 $g/m^2$.

Layers can also be present under the imageable layer to enhance developability or to act as a thermal insulating layer. The underlying layer should be soluble or at least dispersible in the developer and preferably have a relatively low thermal conductivity coefficient.

The various layers may be applied by conventional extrusion coating methods from melt mixtures of the respective layer compositions. Typically such melt mixtures contain no volatile organic solvents.

Intermediate drying steps may be used between applications of the various layer formulations to remove solvent(s) before coating other formulations. Drying steps at conventional times and temperatures may also help in preventing the mixing of the various layers.

Once the various layers have been applied and dried on the substrate, the imageable element can be enclosed in water-impermeable material that substantially inhibits the transfer of moisture to and from the imageable element.

By "enclosed", we mean that the imageable element is wrapped, encased, enveloped, or contained in a manner such that both upper and lower surfaces and all edges are within the water-impermeable sheet material. Thus, none of the imageable element is exposed to the environment once it is enclosed.

Useful water-impermeable sheet materials include but are not limited to, plastic films, metal foils, and waterproof papers that are usually in sheet-form and sufficiently flexible to conform closely to the shape of the imageable element (or stack thereof as noted below) including an irregularities in the surfaces. Typically, the water-impermeable sheet material is in close contact with the imageable element (or stack thereof). In addition, it is preferred that this material is sufficiently tight or is sealed, or both, so as to provide a sufficient barrier to the movement or transfer of moisture to or from the imageable element. Useful water-impermeable materials include plastic films such as films composed of low density polyethylene, polypropylene, and poly(ethylene terephthalate), metallic foils such as foils of aluminum, and waterproof papers such as papers coated with polymeric resins or laminated with metal foils (such as paper backed aluminum foil). The plastic films and metallic foils are most preferred. In addition, the edges of the water-impermeable sheet materials can be folded over the edges of the imageable elements and sealed with suitable sealing means such as sealing tape and adhesives.

The transfer of moisture from and to the imageable element is "substantially inhibited", meaning that over a 24-hour period, the imageable element neither loses nor gains no more than 0.01 g of water per $m^2$. The imageable element (or stack) can be enclosed or wrapped while under vacuum to remove most of the air and moisture. In addition to or instead of vacuum, the environment (for example, humidity) of the imageable element can be controlled (for example to a relative humidity of less than 20%), and a desiccant can be associated with the imageable element (or stack).

For example, the imageable element can be enclosed with the water-impermeable sheet material as part of a stack of imageable elements, which stack contains at least 5 imageable elements and more generally at least 100 or at least 500 imageable elements that are enclosed together. It may be desirable to use "dummy", "reject", or non-photosensitive elements at the top and bottom of the stack improve the wrapping. Alternatively, the imageable element can be enclosed in the form of a coil that can be cut into individual elements at a later time. Generally, such a coil has at least 1000 $m^2$ of imageable surface, and commonly at least 3000 $m^2$ of imageable surface.

Adjacent imageable elements in the stacks or adjacent spirals of the coil may be separated by interleaving material, for example interleaving paper or tissue ("interleaf paper") that may be sized or coated with waxes or resin (such as polyethylene) or inorganic particles. Many useful interleaving materials are commercially available. They generally have a moisture content of less than 8% or typically less than 6%.

Imaging Conditions

During use, the imageable element is exposed to a suitable source of imaging or exposing radiation such as near-infrared or infrared radiation, depending upon the radiation absorbing compound present in the radiation-sensitive composition, at a wavelength of from about 650 to about 1500 nm. For example, imaging can be carried out using imaging or exposing radiation, such as from an infrared laser at a wavelength of at least 700 nm and up to and including about 1500 nm and typically at least 700 nm and up to and including 1200 nm. Imaging can be carried out using imaging radiation at multiple wavelengths at the same time if desired.

The laser used to expose the imageable element is usually a diode laser, because of the reliability and low maintenance of diode laser systems, but other lasers such as gas or solid-state lasers may also be used. The combination of power, intensity and exposure time for laser imaging would be readily apparent to one skilled in the art. Presently, high performance lasers or laser diodes used in commercially available imagesetters emit infrared radiation at a wavelength of at least 800 nm and up to and including 850 nm or at least 1060 and up to and including 1120 nm.

The imaging apparatus can function solely as a platesetter or it can be incorporated directly into a lithographic printing press. In the latter case, printing may commence immediately after imaging and development, thereby reducing press set-up time considerably. The imaging apparatus can be configured as a flatbed recorder or as a drum recorder, with the imageable member mounted to the interior or exterior cylindrical surface of the drum. An example of an useful imaging apparatus is available as models of Creo Trendsetter® platesetters available from Eastman Kodak Company (Burnaby, British Columbia, Canada) that contain laser diodes that emit near infrared radiation at a wavelength of about 830 nm. Other suitable imaging sources include the Crescent 42T Platesetter that operates at a wavelength of 1064 nm (available from Gerber Scientific, Chicago, Ill.) and the Screen PlateRite 4300 series or 8600 series platesetter (available from Screen, Chicago, Ill.). Additional useful sources of radiation include direct imaging presses that can be used to image an element while it is attached to the printing plate cylinder. An example of a suitable direct imaging printing press includes the Heidelberg SM74-DI press (available from Heidelberg, Dayton, Ohio).

Imaging with infrared radiation can be carried out generally at imaging energies of at least 30 $mJ/cm^2$ and up to and including 500 $mJ/cm^2$, and typically at least 50 and up to and including 300 $mJ/cm^2$ depending upon the sensitivity of the imageable layer.

While laser imaging is desired in the practice of this invention, imaging can be provided by any other means that provides thermal energy in an imagewise fashion. For example, imaging can be accomplished using a thermoresistive head (thermal printing head) in what is known as "thermal printing", described for example in U.S. Pat. No. 5,488,025 (Martin et al.). Thermal print heads are commercially available (for example, a Fujitsu Thermal Head FTP-040 MCS001 and TDK Thermal Head F415 HH7-1089).

Development and Printing

With or without a pre-heat step after imaging and before development, the imaged elements can be developed "off-press" using conventional processing and a conventional aqueous alkaline or organic solvent-based developer. Alternatively, the imaged elements can be developed, or imaged and developed, "on-press" as described in more detail below.

For off-press development, the developer composition commonly includes one or more ingredients selected from the group consisting of surfactants, chelating agents (such as salts of ethylenediaminetetraacetic acid), organic solvents (such as benzyl alcohol), and alkaline components (such as inorganic metasilicates, organic metasilicates, hydroxides, bicarbonates, organic amines, and sodium triphosphates). The pH of the alkaline developer is typically at least 8 and up to and including 14. The imaged elements are generally developed using conventional processing conditions.

Developers commonly used for conventional negative-working elements may be used. Such developers typically contain organic solvents, surfactants, alkali agents, and other additives such as chelating agents, antifoamants, and algicides. The pH values of such developers are typically in the range of from about 7 to about 12. Useful organic solvents include the reaction products of phenol with ethylene oxide and propylene oxide [such as ethylene glycol phenyl ether (phenoxyethanol)], benzyl alcohol, esters of mono- di-, or triethylene glycol and of mono-, di-, or tripropylene glycol with acids having 6 or less carbon atoms, and ethers of mono-, di-, or triethylene glycol, diethylene glycol, and of mono-, di-, or tripropylene glycol with alkyl groups having 6 or less carbon atoms, such as 2-ethylethanol and 2-butoxyethanol. The organic solvent(s) is generally present in an amount of from about 0.5 to about 15% based on total developer weight.

Representative developers used for conventional negative-working elements include ND-I Developer, Developer 980, SP 200 Developer, "2-in-1" Developer, ProNeg D-501 Developer, 955 Developer, and 956 Developer (available from Kodak Polychrome Graphics a subsidiary of Eastman Kodak Company).

Developers commonly used for developing conventional positive-working elements may also be used. Such developers typically contain alkali agents (such as alkali metal silicate or metasilicates, alkali metal hydroxides, alkali metal triphosphates, and alkali metal carbonates), and optional additives such as surfactants, anticorrosion agents, chelating agents, antifoamants, and coating protection agents. Such developers generally have a pH of at least 11 and typically of at least 13. Useful developers of this type include 3000 Developer, 9000 Developer, GOLDSTAR Developer, GREENSTAR Developer, ThermalPro Developer, PROTHERM Developer, MX1813 Developer, TCD-300 Developer, and MX1710 Developer (all available from Kodak Polychrome Graphics, a subsidiary of Eastman Kodak Company).

Generally for off-press development, the alkaline developer is applied to the imaged element by rubbing or wiping the outer layer with an applicator containing the developer. Alternatively, the imaged element can be brushed with the developer or the developer may be applied by spraying the outer layer with sufficient force to remove the exposed regions. Still again, the imaged element can be immersed in the developer. In all instances, a developed image is produced in a lithographic printing plate having excellent resistance to press room chemicals.

Following off-press development, the imaged element can be rinsed with water and dried in a suitable fashion. The dried element can also be treated with a conventional gumming solution (preferably gum arabic). In addition, a postbake operation can be carried out, with or without a blanket exposure to UV or visible radiation.

Printing can be carried out by applying a lithographic printing ink and fountain solution to the printing surface of the imaged and developed element. The fountain solution is taken up by the non-imaged regions, that is, the surface of the hydrophilic substrate revealed by the imaging and development steps, and the ink is taken up by the imaged (non-removed) regions of the imaged layer. The ink is then transferred to a suitable receiving material (such as cloth, paper, metal, glass, or plastic) to provide a desired impression of the image thereon. If desired, an intermediate "blanket" roller can be used to transfer the ink from the imaged member to the receiving material. The imaged members can be cleaned between impressions, if desired, using conventional cleaning means.

Some imageable elements of this invention are designed for development "on-press". This type of development avoids the use of the developing solutions described above. The imaged element is directed mounted on press wherein the unexposed regions in the imageable layer are removed by a suitable fountain solution, lithographic printing ink, or a combination of both, when the initial printed impressions are made. Typical ingredients of aqueous fountain solutions include pH buffers, desensitizing agents, surfactants and wetting agents, humectants, low boiling solvents, biocides, antifoaming agents, and sequestering agents. A representative example of a fountain solution is Varn Litho Etch 142W+Varn PAR (alcohol sub)(available from Varn International, Addison, Ill.).

The following examples are provided to illustrate the practice of the invention but are by no means intended to limit the invention in any manner.

EXAMPLES

The components and materials used in the examples and synthetic methods used in evaluation were as follows:

AIBN represents azobis(iso-butyroInitrile) that was obtained from Jyunsei Chemical Company, Ltd. (Japan).

AMA represents allyl methacrylate that is available from TCI (Japan).

AN represents acrylonitrile that is available from TCI.

Contrast Dye D11 is ethanaminium, N-[4-[[4-(diethylamino)phenyl][4-(ethylamino)-1-naphthalenyl]methylene]-2,5-cyclohexadien-1-ylidene]-N-ethyl-, salt with 5-benzoyl-4-hydroxy-2-methoxybenzenesulfonic acid (1:1) and is available from Hodogaya Chemical.

Fluorinated Polymer A represents a fluorinated acrylic polymer having pendant methacryloyl groups useful as an ink-accepting promoting component that was obtained from Shin-nakamura Chemical Corp. (Japan).

DMAc represents N,N-dimethylacetamide.

Initiator C represents bis(t-butylphenyl)iodonium tetraphenyl)borate.

IPA represents iso-propanol.

IR Dye 1 is a cyanine dye that is available from Showa Denko (Tokyo, Japan) and has the following structure:

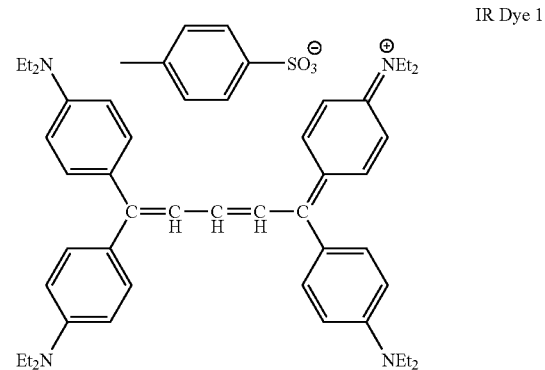

IR Dye 1

Irgacure® 250 is a 75 wt. % solution of iodonium, (4-methoxyphenyl)[4-(2-methylpropyl)phenyl]-, hexafluorophosphate in propylene carbonate that was obtained from Ciba Specialty Chemicals (Tarrytown, N.Y.).

Kayarad DPHA is a dipentaerythyltol hexaacrylate crosslinking agent that is available from Nippon Kayaku KK (Japan).

MEK represents methyl ethyl ketone.

Mercapto-3-triazole represents mercapto-3-triazole-1H, 2, 4 that was obtained from PCAS (Paris, France).

MDP-S represents 2,2'-methylenebis (6-t-butyl-4-methylphenol) is an inhibitor that was obtained from Sumitomo Chemical (Japan).

$NaBPh_4$ represents sodium tetraphenyl borate that is available from TCI (Japan).

Newcol 2305 and 2320 are polyethyleneoxide mono alkyl ether surfactants that were obtained from Nippon Nyukazai (Japan).

P3B has the following formula and was obtained from Showa Denko:

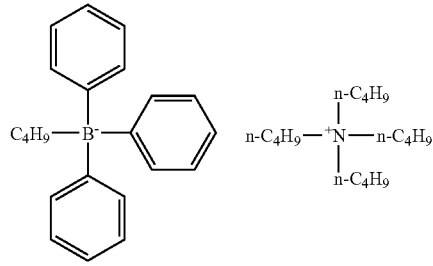

P3B

Paintad 19 is a surfactant equivalent to DC-190 that is available from Dow Chemical Company (Midland, Mich.).

PF represents a post-treatment with an inorganic monosodium phosphate solution activated by sodium fluoride.

PGME represents propyleneglycol monomethylether.

PVA-203 represents a poly(vinyl alcohol) that was obtained from Kuraray (Japan).

PVP K-30 represents a poly(vinyl pyrrolidone) that was obtained from ISP (Texas).

TCD-300 Developer (diluted ratio is 1+4 by water) is available from Eastman Kodak Company.

TCP represents tricresil phosphate that is available from Sumitomo chemical (Japan).

Polyonium Compound A is a diiodonium compound having the following formula:

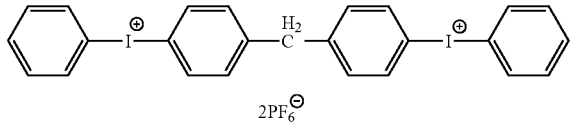

Polyonium Compound B is a triiodonium compound having the following formula:

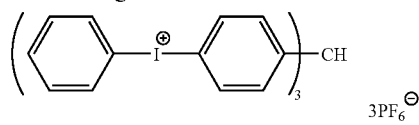

Acrylic Binder A is an acrylic polymer having pendant allyl groups that was prepared in the following manner:

A 300-ml, four-necked, round-bottom flask, fitted with a mechanical stirrer, reflux condenser, and thermometer, nitrogen inlet adapter, and a dropping funnel, was placed under a nitrogen atmosphere and charged with DMAc (100 g). A solution of AMA (8 g), AN (6 g), N-benzoic acid methacrylamide (6 g), and AIBN (0.4 g) in DMAc (80 g) was added dropwise via the dropping funnel over 2 hours at 80° C. The resulting reaction mixture was stirred at the same temperature for 6 hours while adding AIBN (0.2 g) every hour. For workup, the reaction mixture was poured into 2 liters of water with stirring. After filtration, the resulting solid was stirred into water and filtered again. The collected solid (Acrylic Binder A) was dried in a vacuum oven after drying at room temperature.

Initiator Syntheses:

Initiator A was prepared using 2-liter and 1-liter beakers equipped with a mechanical stirrer. IPA (600 g), deionized water (400 g), acetone (150 g), and Polyonium Compound A (79.02 g) were stirred together in the 2-liter beaker. IPA (300 g), deionized water (200 g), acetone (75 g), and $NaBPh_4$ (29.6 g) were stirred together in the 1-liter beaker. After the mixture became clear, contents of the 1-liter beaker were poured into the 2-liter beaker. A white crystal formed immediately, and the contents in the 2-liter beaker were stored at 8° C. overnight and filtered and washed by water and filtered again. After drying, the desired Initiator A (58 g) was obtained. From analysis, no phosphorus or fluorine atoms were found in the crystal. Initiator A has the following structure:

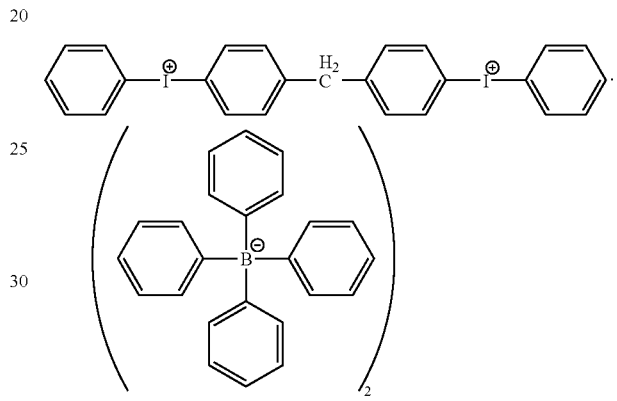

Initiator B was prepared by using 500-ml and 200-ml beakers equipped with a mechanical stirrer. IPA (42.3 g), deionized water (79.2 g), acetone (79.2 g), and Polyonium Compound B (4.38 g) were stirred together in the 500-ml beaker. IPA (21.2 g), deionized water (39.5 g), acetone (39.5 g), and $NaBPh_4$ (3.49 g) were stirred together in the 200-ml beaker. After the mixture became clear, contents of the 200-ml beaker were poured into the 500-ml beaker with strong stirring. A white crystal formed immediately, and the contents in the 2-liter beaker were stored at 8° C. overnight and filtered and washed by water and filtered again. After drying, the desired Initiator B (6.1 g) was obtained. From analysis, no phosphorus or fluorine atoms were found in the crystal. Initiator B has the following structure:

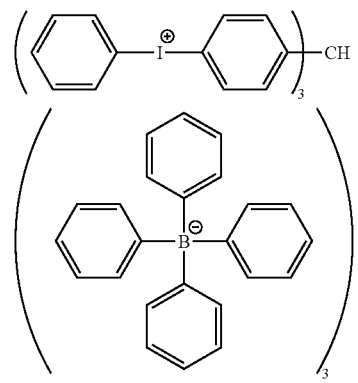

INVENTION EXAMPLES 1 & 2 AND COMPARATIVE EXAMPLES 1 & 2

Imageable elements were prepared by coating the imageable layer formulation shown in the following TABLE I with the initiators shown in TABLE II below onto an electrochemically-grained and sulfuric acid-anodized aluminum support to provide dry imageable layer coverage of 1.3 g/m². Each imageable layer formulation was applied using a #9 coating rod and dried for 60 seconds at 110° C.

The protective overcoat formulation shown in TABLE III below was then applied to the dried imageable layer to provide a dry coverage of 0.5 g/m² after drying at 110° C. for 60 seconds.

Each of the resulting imageable elements was exposed at 120 mJ/cm² on a PTR-4300 Model imagesetter (Screen, Chicago, Ill.). The imaged elements were then developed with TCD-303 1+4 in a PK-1310 processor at 30° C. The resulting printing plates were rubbed thoroughly and evaluated to provide the results shown below in TABLE IV.

TABLE IV

| Example | Development Time | Image Area OD* | Smallest Snail Plugging** | Developability after "HT" test*** | IR Speed after "HT" test |
|---|---|---|---|---|---|
| Invention 1 | 16-17 seconds | 2.160 | 136 mJ/cm² | Slightly slower | Not changed |
| Invention 2 | 20 seconds | 2.162 | 136 mJ/cm² | Slightly slower | Not changed |
| Comparative 1 | 16-17 seconds | 2.138 | 128 mJ/cm² | Slightly slower | Not changed |
| Comparative 2 | 15 seconds | 2.09 | 112 mJ/cm² | Slower | Severely reduced |

*"OD" refers to optical density and was measured using X-Rite Model 528 machine (X-Rite Inc. Grandville, MI).

**Snail plugging refers to the small imaging pattern on the test chart of a commercial PTR-4300 plate setter. If the dot gain from imaging is large enough, the snail pattern can't be produced. So a printing plate that shows snail plugging with less IR imaging power tends to have a large dot gain.

***The "HT" test was performed at 38° C./80% RH for 7 days followed by development to evaluate the developability and imaging speed ("IR speed").

The results shown in TABLE IV indicate that the imageable elements in Invention Examples 1 and 2 provide printing plates with long press life and small dot gain compared to the printing plates from the Comparative Examples. Because the invention printing plates showed "high image area OD", the imaged layer after development was thick and provided long press life. The smaller snail plugging obtained with Invention Examples 1 and 2 occurred at higher imaging power, indicating that the dot gain from IR imaging was smaller than that obtained from the Comparative Examples at the same imaging power. In addition, the Invention Examples 1 and 2 also provided printing plates with long shelf life as evidenced by the good results from the "HT" accelerated aging test.

The invention has been described in detail with particular reference to certain preferred embodiments thereof, but it will be understood that variations and modifications can be effected within the spirit and scope of the invention.

TABLE I

| Component | Amount (g) |
|---|---|
| PGME | 68.8 |
| MEK | 68.8 |
| Acrylic Binder A | 5.64 |
| Kayarad DPHA | 3.96 |
| First Initiator | See TABLE II |
| Second Initiator | See TABLE II |
| IR Dye 1 | 0.386 |
| MDP-S | 0.103 |
| TCP | 0.368 |
| Fluorinated Polymer A | 0.185 |
| Paintad 19 | 0.504 |
| D11 | 0.368 |

TABLE II

| Example | First Initiator | Amount (g) | Second Initiator | Amount (g) |
|---|---|---|---|---|
| Invention 1 | A | 0.733 | None | 0 |
| Invention 2 | B | 0.733 | None | 0 |
| Comparative 1 | C | 0.891 | None | 0 |
| Comparative 2 | Irgacure ® 250 | 0.748 | P3B | 0.141 |

TABLE III

| Component | Amount (g) |
|---|---|
| De-ionized water | 96.0 |
| PVA-203 | 2.608 |
| PVP K-30 | 0.870 |
| Sodium p-toluenesulfonic acid | 0.174 |
| Newcol 2320 | 0.232 |
| Newcol 2305 | 0.116 |

The invention claimed is:

1. An infrared radiation-sensitive imageable element comprising a substrate having thereon an imageable layer comprising:
   a free radically polymerizable component,
   an initiator composition capable of generating free radicals sufficient to initiate polymerization of said free radically polymerizable component upon exposure to imaging radiation,
   an infrared radiation absorbing compound, and
   a polymeric binder,
   wherein said initiator composition comprises a polyonium borate comprising a polyiodonium cation and sufficient organic borate counterions to provide a net neutral charge.

2. The imageable element of claim 1 wherein said organic borate counterions comprise the same alkyltriarylborate or tetraarylborate counterions, wherein the aryl groups are optionally substituted with one or more alkyl, alkoxy, halo, or haloalkyl groups.

3. The imageable element of claim 1 comprising one or more of the polyiodonium borate salts represented by the following Structures (I):

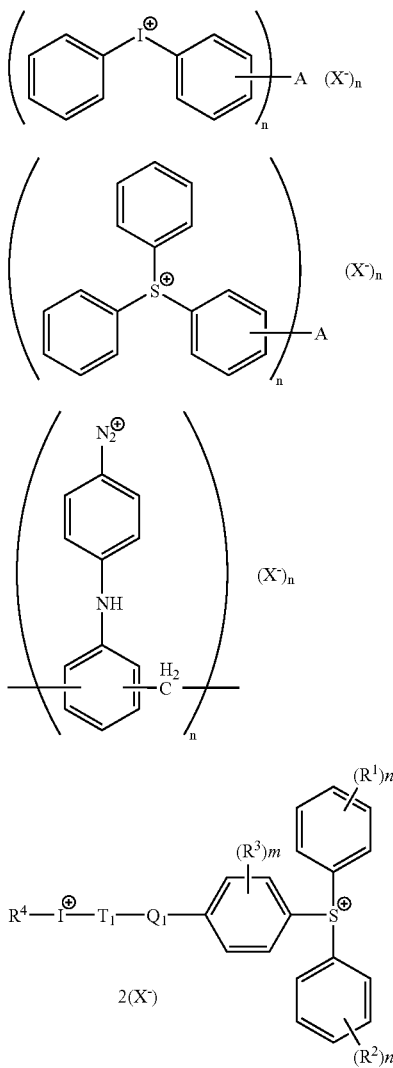

wherein n is at least 2, A represents (n-1) connecting groups connecting onium moieties, $X^-$ represents the same or different organic borate counterions selected from polyalkyl-, polyaryl-, or alkylarylborate cations, and wherein any of the phenyl rings in Structure (I) can be substituted with one or more substituents.

4. The imageable element of claim 3 wherein $X^-$ represents the same or different tetraphenyl borate or alkyltriphenyl borate wherein the phenyl groups are optionally substituted with one or more halo or haloalkyl groups.

5. The imageable element of claim 1 wherein said polyonium borate salt is a polyiodonium tetraaryl borate salt.

6. The imageable element of claim 1 wherein said initiator composition further comprises a mercaptotriazole or a metallocene.

7. The imageable element of claim 1 wherein said imageable layer further comprises a colorant.

8. The imageable element of claim 1 that is on-press developable.

9. The imageable element of claim 1 further comprising an oxygen-barrier overcoat disposed on said imageable layer.

10. The imageable element of claim 1 wherein said infrared radiation absorbing compound is an infrared radiation dye.

11. A method comprising:
    A) imagewise exposing the imageable element of claim 1 using imaging infrared radiation to produce exposed and non-exposed regions, and
    B) developing said imagewise exposed element to remove only said non-exposed regions.

12. The method of claim 11 wherein developing step B is carried out on-press in the presence of a fountain solution, lithographic printing ink, or a combination thereof, after imagewise exposure using an infrared laser.

13. The method of claim 11 wherein developing step B is carried out off-press using an aqueous alkaline developer after imagewise exposure using an infrared laser.

* * * * *

UNITED STATES PATENT AND TRADEMARK OFFICE
CERTIFICATE OF CORRECTION

PATENT NO. : 7,862,984 B2
APPLICATION NO. : 11/692255
DATED : January 4, 2011
INVENTOR(S) : Hayashi et al.

It is certified that error appears in the above-identified patent and that said Letters Patent is hereby corrected as shown below:

In Column 38, Claim 3, line 67, delete "Structures" and insert -- Structure --.

In Column 39, delete the structure

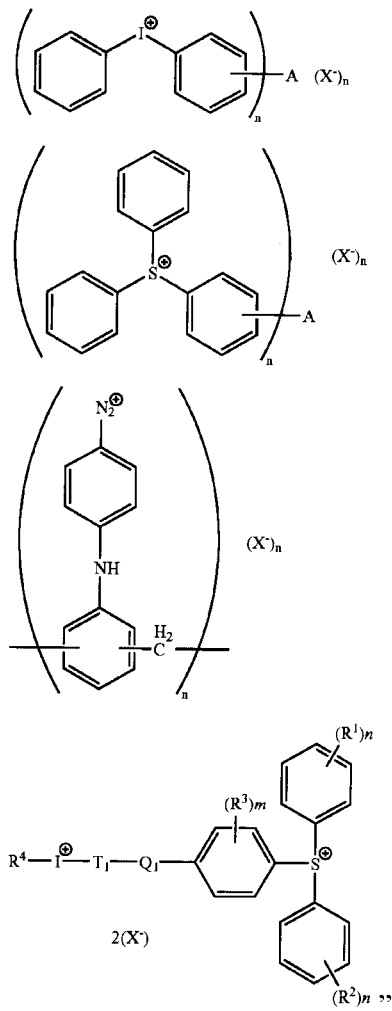

" "

Signed and Sealed this
Ninth Day of April, 2013

Teresa Stanek Rea
*Acting Director of the United States Patent and Trademark Office* and insert
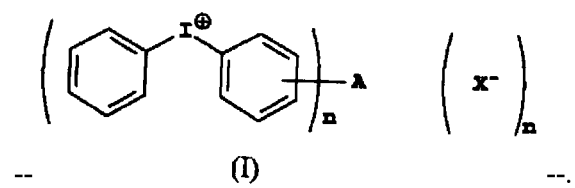
-- (I) --.